US012805463B2

(12) United States Patent
Atwood et al.

(10) Patent No.: US 12,805,463 B2
(45) Date of Patent: Nov. 24, 2026

(54) **CLUBROOT RESISTANCE IN *Brassica***

(71) Applicant: PIONEER HI-BRED INTERNATIONAL, INC., Johnston, IA (US)

(72) Inventors: Sarah Atwood, Ankeny, IA (US); Sunita R Chilakamarri, Waukee, IA (US); Igor Falak, Guelph (CA); Xiuqiang Huang, Mississauga (CA); Siva S. Ammiraju Jetty, Johnston, IA (US); Jonathan Myrvold, Lompoc, CA (US); Joshua Michael Shendelman, Ankeny, IA (US)

(73) Assignee: PIONEER HI-BRED INTERNATIONAL, INC., Johnston, IA (US)

(*) Notice: Subject to any disclaimer, the term of this patent is extended or adjusted under 35 U.S.C. 154(b) by 295 days.

(21) Appl. No.: 18/262,995

(22) PCT Filed: Jan. 24, 2022

(86) PCT No.: PCT/US2022/013522
§ 371 (c)(1),
(2) Date: Jul. 26, 2023

(87) PCT Pub. No.: WO2022/164752
PCT Pub. Date: Aug. 4, 2022

(65) Prior Publication Data

US 2024/0090396 A1 Mar. 21, 2024

Related U.S. Application Data

(60) Provisional application No. 63/142,717, filed on Jan. 28, 2021.

(51) Int. Cl.
*A01H 1/04* (2006.01)
*A01H 1/00* (2006.01)
*C12Q 1/6895* (2018.01)

(52) U.S. Cl.
CPC ........... *A01H 1/045* (2021.01); *A01H 1/1245* (2021.01); *C12Q 1/6895* (2013.01); *C12Q 2600/13* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS

| | | | |
|---|---|---|---|
| 2014/0289900 A1 | 9/2014 | Poraty-Gavra et al. | |
| 2017/0159067 A1 | 6/2017 | Charne et al. | |
| 2018/0305774 A1 | 10/2018 | Christianson et al. | |
| 2020/0283806 A1 | 9/2020 | Koch et al. | |

FOREIGN PATENT DOCUMENTS

| | | |
|---|---|---|
| KR | 102116428 B1 | 5/2020 |
| WO | WO-2020168166 A2 | 8/2020 |

OTHER PUBLICATIONS

Werner et al. Theor Appl Genet (2008) 116:363-373.*
Werner et al. Theor Appl Genet (2008)116:363-372.*
Anonymous., "Canola Trait Polymorphisms and Sequences to Detect," Research Disclosure, 2015, vol. 61, No. 32, XP007144564, ISSN: 0374-4353, 12 Pages.
Karim M.M., et al., "Two Clubroot-Resistance Genes, Rcr3 and Rcr9wa, Mapped in *Brassica rapa* Using Bulk Segregant RNA Sequencing," International Journal of Molecular Sciences, 2020, vol. 21, No. 14, p. 5033, XP093223878, ISSN: 1422-0067, pp. 1-15.
Piao Z., et al., "Genetics of Clubroot Resistance in *Brassica* Species," Journal of Plant Growth Regulation, 2009, vol. 28, No. 3, pp. 252-264, XP019739174.
Chen J. et al., "Identification of Novel QTLs for Isolate-Specific Partial Resistance to Plasmodiophora brassicae in *Brassica rapa*" PLoS ONE, Dec. 20, 2013, vol. 8(12), pp. 1-12, e85307. doi:10.1371/journal.pone.0085307.
Chu M. et al., "Fine mapping of Rcr1 and analyses of its effect on transcriptome patterns during infection by Plasmodiophora brassicae" BMC Genomics, Dec. 23, 2014, vol. 15(1):1166, pp. 1-20, doi: 10.1186/1471-2164-15-1166.
Hirai M. et al., "A novel locus for clubroot resistance in *Brassica rapa* and its linkage markers" Theor Appl Genet, Feb. 2004, vol. 108(4), pp. 639-643. doi: 10.1007/s00122-003-1475-x. Epub Oct. 10, 2003.
International Preliminary Report on Patentability for International Application No. PCT/US2022/013522, mailed Aug. 10, 2023, 9 Pages.
Matsumoto E. et al., "Linkage analysis of RFLP markers for clubroot resistance and pigmentation in Chinese cabbage (*Brassica rapa* ssp. *pekinensis*)" Euphytica Dec. 1998 104, pp. 79-86.
Mehraj H. et al., "Genetics of Clubroot and Fusarium Wilt Disease Resistance in *Brassica* Vegetables: The Application of Marker Assisted Breeding for Disease Resistance", Plants, Jun. 9, 2020, pp. 1-15. DOI: 10.3390/plants9060726.
Pang W. et al., "Identification and Mapping of the Clubroot Resistance Gene CRd in Chinese Cabbage (*Brassica rapa* ssp. *pekinensis*)" Front Plant Sci, May 18, 2018, vol. 9, Article.653, pp. 1-9. doi: 10.3389/fpls.2018.00653.
Piao Z.Y. et al., "SCAR and CAPS mapping of CRb, a gene conferring resistance to Plasmodiophora brassicae in Chinese cabbage (*Brassica rapa* ssp. *pekinensis*)" Theor Appl Genet, May 2004, vol. 108(8), pp. 1458-1465. doi: 10.1007/s00122-003-1577-5. Epub Mar. 2, 2004.

(Continued)

*Primary Examiner* — Medina A Ibrahim

(57) ABSTRACT

Provided are methods and compositions, including assays, probes and primers for identifying *Brassica* plants that are resistant to clubroot disease. Also provided are breeding methods for introducing a clubroot resistance phenotype into *Brassica* plants and/or their progeny.

10 Claims, No Drawings

Specification includes a Sequence Listing.

(56) References Cited

OTHER PUBLICATIONS

Saito M. et., "Fine mapping of the clubroot resistance gene, Crr3, in *Brassica rapa*" Theor Appl Genet. Dec. 2006; vol. 114(1): pp. 81-91. doi: 10.1007/s00122-006-0412-1. Epub Oct. 13, 2006.
Sakamoto K. et al., "Mapping of isolate-speciWc QTLs for clubroot resistance in Chinese cabbage (*Brassica rapa* L. *ssp. pekinensis*)" Theor Appl Genet, Sep. 2008; vol. 117(5):759-67. doi: 10.1007/s00122-008-0817-0. Epub Jul. 9, 2008.
Suwabe K. et al., "Identification of two loci for resistance to clubroot (*Plasmodiophora brassicae* Woronin) in *Brassica rapa* L." Theor Appl Genet. Oct. 2003; vol. 107(6): pp. 997-1002. doi: 10.1007/s00122-003-1309-x. Epub Jun. 14, 2003.
Yu F. et al., "Genotyping-by-sequencing reveals three QTL for clubroot resistance to six pathotypes of Plasmodiophora brassicae in *Brassica rapa*" Sci Rep, Jul. 3, 2017; vol. 7(1):4516, pp. 1-11. doi: 10.1038/s41598-017-04903-2.

* cited by examiner

SEQUENCE LISTING

<160> NUMBER OF SEQ ID NOS: 330

<210> SEQ ID NO 1
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 1
tctctctaca gttttgg 17

<210> SEQ ID NO 2
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 2
tctctaccgt tttggtg 17

<210> SEQ ID NO 3
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 3
caatttcatt atcgtatctg caaatt 26

<210> SEQ ID NO 4
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 4
tatgcggcat tggtttcttg 20

<210> SEQ ID NO 5
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 5
atggtgttac tccgcct 17

<210> SEQ ID NO 6
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 6
atggtgttac accgcc 16

<210> SEQ ID NO 7
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 7
agtggaagag ttccctgatg ag 22

<210> SEQ ID NO 8
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 8
tggaccacta taaacgaggc taa 23

<210> SEQ ID NO 9
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 9
acgaggctaa tatattcact attggag 27

<210> SEQ ID NO 10
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 10
acctacgata tatggttcag tggaa 25

<210> SEQ ID NO 11
<211> LENGTH: 16
<212> TYPE: DNA

<213> ORGANISM: Artificial Sequence
<220> FEATURE:
<223> OTHER INFORMATION: synthetic oligonucleotide

<400> SEQUENCE: 11
caccactttg ttaaaa 16

<210> SEQ ID NO 12
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 12
caccactttg tcaaaa 16

<210> SEQ ID NO 13
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 13
ggtggttttg cccttgtaaa 20

<210> SEQ ID NO 14
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 14
ccaaattctg gttcttctga caa 23

<210> SEQ ID NO 15
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 15
ctacagtata aatttccac 19

<210> SEQ ID NO 16
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 16
cctacagtat aaatctc 17

<210> SEQ ID NO 17
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 17
ccttagaaat ttcacacaag ttgatt 26

<210> SEQ ID NO 18
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 18
caagttcttt aaggaaagag agaggtt 27

<210> SEQ ID NO 19
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 19
gaaggaacct tagaaatttc acaca 25

<210> SEQ ID NO 20
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 20
attctcatcg catctt 16

<210> SEQ ID NO 21
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 21
tctcatcgga tcttt 15

<210> SEQ ID NO 22
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 22
cacgttttgt ttacatcg 18

<210> SEQ ID NO 23
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 23
cacgttttgt ttcca 15

<210> SEQ ID NO 24
<211> LENGTH: 26
<212> TYPE: DNA
<213> ORGANISM: Artificial Sequence
<220> FEATURE:

<223> OTHER INFORMATION: synthetic oligonucleotide

<400> SEQUENCE: 24
aataggctta tcacctcctt gtttaa 26

<210> SEQ ID NO 25
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 25
ggcagaagtg gatggggta 19

<210> SEQ ID NO 26
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 26
gcaactaata ggcttatcac ctcctt 26

<210> SEQ ID NO 27
<211> LENGTH: 14
<212> TYPE: DNA
<213> ORGANISM: Artificial Sequence
<220> FEATURE:
<223> OTHER INFORMATION: synthetic oligonucleotide

<400> SEQUENCE: 27
atcgctcctg caac 14

<210> SEQ ID NO 28
<211> LENGTH: 14
<212> TYPE: DNA
<213> ORGANISM: Artificial Sequence
<220> FEATURE:
<223> OTHER INFORMATION: synthetic oligonucleotide

<400> SEQUENCE: 28
atcgctcccg caac 14

<210> SEQ ID NO 29
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 29
atctgtacat gtgaaaca 18

<210> SEQ ID NO 30
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 30
atctgtacat gagaaac 17

<210> SEQ ID NO 31
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 31
aacaagtgtg attctcattt ccaa 24

<210> SEQ ID NO 32
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 32
tgagatgaag acacattcac aca 23

<210> SEQ ID NO 33
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 33
ttgtttaaac tctggttcc 19

<210> SEQ ID NO 34
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 34
ttgtttaagc tctggttc 18

<210> SEQ ID NO 35
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 35
gtgtcccacc attctctgct 20

<210> SEQ ID NO 36
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 36
tcaattggta gttataatgt tgtgagc 27

<210> SEQ ID NO 37
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 37
ttccacttgt cttgatg 17

<210> SEQ ID NO 38
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 38
ttccacttgt ctcgatg 17

<210> SEQ ID NO 39
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 39
cttatatcaa tcgtgatttc 20

<210> SEQ ID NO 40
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 40
ctcttatatc aatcatgatt tc 22

<210> SEQ ID NO 41
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 41
ctcgatccat aatgtttcta atcaaaaggc 30

<210> SEQ ID NO 42
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 42
cctcagattc ccttatcttg tcgat 25

<210> SEQ ID NO 43
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 43
cctcacaaaa caaag 15

<210> SEQ ID NO 44
<211> LENGTH: 17

<212> TYPE: DNA
<213> ORGANISM: Artificial Sequence
<220> FEATURE:
<223> OTHER INFORMATION: synthetic oligonucleotide

<400> SEQUENCE: 44
tccctcacaa tacaaag 17

<210> SEQ ID NO 45
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 45
ccaaaggatg tgacagagag gtaaa 25

<210> SEQ ID NO 46
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 46
acagatgaac aaaacatgat ataacagact ctt 33

<210> SEQ ID NO 47
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 47
ttttagttaa cattgattta ttac 24

<210> SEQ ID NO 48
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 48
attttagtta acattgattt gttac 25

<210> SEQ ID NO 49
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 49
ctgttgagaa aaaatctaac aaaatcttac ttaaaaattt 40

<210> SEQ ID NO 50
<211> LENGTH: 47
<212> TYPE: DNA
<213> ORGANISM: Artificial Sequence
<220> FEATURE:
<223> OTHER INFORMATION: synthetic oligonucleotide

<400> SEQUENCE: 50
cacatatcac ttctattttt atataatacc gaatagaatt atagaat 47

<210> SEQ ID NO 51
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 51
tccggagtaa agagtg 16

<210> SEQ ID NO 52
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 52
ccggagtgaa gagtg 15

<210> SEQ ID NO 53
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 53
gcctctttta ggtttgggtt gga 23

<210> SEQ ID NO 54
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 54
ccggcccaga tgggttaaa 19

<210> SEQ ID NO 55
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 55
cttagttttg gaacgcacca 20

<210> SEQ ID NO 56
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 56
cttagttttg gaacgcatca 20

<210> SEQ ID NO 57
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 57
cccacggaaa agtctataca actga 25

<210> SEQ ID NO 58
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 58
gtcgtcgtgg ttgtgatgat atct 24

<210> SEQ ID NO 59
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 59
tggcgtataa gaagcaataa 20

<210> SEQ ID NO 60
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 60
tggcgtataa gaaacaataa 20

<210> SEQ ID NO 61
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 61
tcaatactag gtatatacat acttgtttgc taagtga 37

<210> SEQ ID NO 62
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 62
ctagagtgtc tacgcatttt gaagaga 27

<210> SEQ ID NO 63
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 63
acactcagca aagca 15

<210> SEQ ID NO 64
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 64
cacactcaac aaagca 16

<210> SEQ ID NO 65
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 65
gcaaataaca aatccagaca gaaccaa 27

<210> SEQ ID NO 66
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 66
tgcaaccttg tcctatcagt tcaat 25

<210> SEQ ID NO 67
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 67
aaacttgttt atttttcg 18

<210> SEQ ID NO 68
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 68
caaacttgtt tagttttcg 19

<210> SEQ ID NO 69
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 69
atcttcacat tcctgcattg tttttgtt 28

<210> SEQ ID NO 70
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 70
attgttgaaa gttttagctg tttcaaatta acat 34

<210> SEQ ID NO 71
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 71
ttcgatttat ctcttttttt t 21

<210> SEQ ID NO 72
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 72
tttcgattta tctctctttt tt 22

<210> SEQ ID NO 73
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 73
agactgcggt atcaggtaaa aacaa 25

<210> SEQ ID NO 74
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 74
cgaactcgag agccaatcca aatt 24

<210> SEQ ID NO 75
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 75
tttagtagcc aatcatgatt 20

<210> SEQ ID NO 76
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 76
tttagtagcc agtcatgatt 20

<210> SEQ ID NO 77

<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 77
cgttaacatt tcattggtta aattagcgtt t 31

<210> SEQ ID NO 78
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 78
catattacgg tttatcttgg gtaagaggtt aaat 34

<210> SEQ ID NO 79
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 79
caccaagaaa caaaaa 16

<210> SEQ ID NO 80
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 80
catcaccaag aaacgaaaa 19

<210> SEQ ID NO 81
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 81
cggaaggatg atgatgaagt gaaatac 27

<210> SEQ ID NO 82
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 82
gattcagttt cgcttcatct tcgtt 25

<210> SEQ ID NO 83
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 83
actgaatcaa aacaaaag 18

<210> SEQ ID NO 84
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 84
actgaatcaa agcaaaag 18

<210> SEQ ID NO 85
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 85
acagattcta caggatcatc accaaga 27

<210> SEQ ID NO 86
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 86
gcttcgattg atctggattc aagct 25

<210> SEQ ID NO 87
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 87
cacattttca aattatg 17

<210> SEQ ID NO 88
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 88
agtcacattt ttaaattatg 20

<210> SEQ ID NO 89
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 89
agtaacgcgg atttgtgagt caa 23

<210> SEQ ID NO 90
<211> LENGTH: 17
<212> TYPE: DNA

<213> ORGANISM: Artificial Sequence
<220> FEATURE:
<223> OTHER INFORMATION: synthetic oligonucleotide

<400> SEQUENCE: 90
gccgggctgt cagtaca 17

<210> SEQ ID NO 91
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 91
ttgaagcctg tattttagt 19

<210> SEQ ID NO 92
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 92
ttgaagcctg tagtttagt 19

<210> SEQ ID NO 93
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 93
gcgttttaac ttttaagagg tagcttgt 28

<210> SEQ ID NO 94
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 94
ggccgggctg tcagtac 17

<210> SEQ ID NO 95
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 95 cagattttg gtattgtttt 20

<210> SEQ ID NO 96
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 96
tttcagattt ttggttttgt ttt 23

<210> SEQ ID NO 97
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 97
cccgataatt aataaaaccc caatgcaa 28

<210> SEQ ID NO 98
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 98
ccgtcgaatt cagtttggtt gattt 25

<210> SEQ ID NO 99
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 99
ctgatgttcg ttctatgtc 19

<210> SEQ ID NO 100
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 100
actgatgttc gttttatgtc 20

<210> SEQ ID NO 101
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 101
gaatacaaaa attcttcaac ttgaaacttt ggac 34

<210> SEQ ID NO 102
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 102
actagcagca aaatatcaaa atttcaaagc a 31

<210> SEQ ID NO 103
<211> LENGTH: 19
<212> TYPE: DNA
<213> ORGANISM: Artificial Sequence
<220> FEATURE:

<223> OTHER INFORMATION: synthetic oligonucleotide

<400> SEQUENCE: 103
tcaaatagga gacgcatct 19

<210> SEQ ID NO 104
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 104
caaataggag gcgcatct 18

<210> SEQ ID NO 105
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 105
gaggcattct cctctttcac ca 22

<210> SEQ ID NO 106
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 106
ctggaatcaa ttacatcaca actttatcag 30

<210> SEQ ID NO 107
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 107
ttttaattat tcagattatt ttt 23

<210> SEQ ID NO 108
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 108
atttttaatt attcaaatta ttttt 25

<210> SEQ ID NO 109
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 109
tctttattaa acggaagaag tatgtaatt 29

<210> SEQ ID NO 110
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 110
ctgcaatttg gttcagaaaa taaaacttct agtaa 35

<210> SEQ ID NO 111
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 111
cgaaaacccg aaacc 15

<210> SEQ ID NO 112
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 112
ccgaaaaacc gaaacc 16

<210> SEQ ID NO 113
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 113
ggctgggctt gtacacatgt taata 25

<210> SEQ ID NO 114
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 114
cttaacacat tgggcctcaa agg 23

<210> SEQ ID NO 115
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 115
accttgttgt acttagca 18

<210> SEQ ID NO 116
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 116 atacttgtt gtagttagca 20

<210> SEQ ID NO 117
<211> LENGTH: 41
<212> TYPE: DNA
<213> ORGANISM: Artificial Sequence
<220> FEATURE:
<223> OTHER INFORMATION: synthetic oligonucleotide

<400> SEQUENCE: 117
tgataaaaag atttaggata tattacaaaa cttgaccatc a 41

<210> SEQ ID NO 118
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 118
cattgtagat gcctagggtt taaaagtcta t 31

<210> SEQ ID NO 119
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 119
catatgacca aattttttt 19

<210> SEQ ID NO 120
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 120
catatgacca aaattttttt 19

<210> SEQ ID NO 121
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 121
caaaacttga ccatcaatac cttgttgt 28

<210> SEQ ID NO 122
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 122
gccattgtag atgcctaggg tttaa 25

<210> SEQ ID NO 123
<211> LENGTH: 26

<212> TYPE: DNA
<213> ORGANISM: Artificial Sequence
<220> FEATURE:
<223> OTHER INFORMATION: synthetic oligonucleotide

<400> SEQUENCE: 123
attttaaaaa atttattatt aatttt 26

<210> SEQ ID NO 124
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 124
ttttaaaaaa tttattgtta atttt 25

<210> SEQ ID NO 125
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 125
ttgtttaata aatcagtttt tatgggttaa 30

<210> SEQ ID NO 126
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 126
tcaacttaaa gattttcaga tttgtagata atttttgtta 40

<210> SEQ ID NO 127
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 127
ttttcaacaa ctattcttg 19

<210> SEQ ID NO 128
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 128
attttttcaa caattattct tg 22

<210> SEQ ID NO 129
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 129
ggaggccacc tggacatt 18

<210> SEQ ID NO 130
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 130
aagaaatatt tttattatca gatgactatt ccgtgtttat ataca 45

<210> SEQ ID NO 131
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 131
atactgggaa aattt 15

<210> SEQ ID NO 132
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 132
catatatact ggaaaaattt 20

<210> SEQ ID NO 133
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 133
acttacaaaa tatgtatcct gacttttcat ggt 33

<210> SEQ ID NO 134
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 134
agtatgagat tgattgggtt tataaatatt atata 35

<210> SEQ ID NO 135
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 135
cccaaaggat ctaagaaa 18

<210> SEQ ID NO 136
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 136
cccaaaggat gtaagaaa 18

<210> SEQ ID NO 137
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 137
tttatgcaat cattggcaac acaca 25

<210> SEQ ID NO 138
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 138
ccagccgaga aagacaactt ga 22

<210> SEQ ID NO 139
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 139
cgtccaaata tattggtgga g 21

<210> SEQ ID NO 140
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 140
agacgtccaa atatattagt ggag 24

<210> SEQ ID NO 141
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 141
tggaggacca gattctgttt gg 22

<210> SEQ ID NO 142
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 142
tggcgaaaaa gtctttatcc tttaatttga c 31

<210> SEQ ID NO 143
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 143
atttgttctc cctcacaata 20

<210> SEQ ID NO 144
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 144
atttgttctc ccacacaata 20

<210> SEQ ID NO 145
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 145
caagcagtgg actatggttg gtta 24

<210> SEQ ID NO 146
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 146
gagaaccttc ctctgtttca aacct 25

<210> SEQ ID NO 147
<211> LENGTH: 14
<212> TYPE: DNA
<213> ORGANISM: Artificial Sequence
<220> FEATURE:
<223> OTHER INFORMATION: synthetic oligonucleotide

<400> SEQUENCE: 147
tccatcgcat tttt 14

<210> SEQ ID NO 148
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 148
ctttccatca cattttt 17

<210> SEQ ID NO 149
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 149
gcatgctgac gtaaacaact acatt 25

<210> SEQ ID NO 150
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 150
cgaataactg agtcacgctt cct 23

<210> SEQ ID NO 151
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 151
aagttactca gacactctac 20

<210> SEQ ID NO 152
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 152
caaagttact cagactctct ac 22

<210> SEQ ID NO 153
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 153
tggtatgtgt ggagagtctg aagtt 25

<210> SEQ ID NO 154
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 154
acacgattgt ggacggatga attat 25

<210> SEQ ID NO 155
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 155
ctgattcacc tctctcgac 19

<210> SEQ ID NO 156

<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 156
ctgattcacc tccctcgac 19

<210> SEQ ID NO 157
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 157
gtgtccacat gctcaagagg tt 22

<210> SEQ ID NO 158
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 158
gtatgctgca aatcgatcag atgtg 25

<210> SEQ ID NO 159
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 159
tccactggct tctcgtta 18

<210> SEQ ID NO 160
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 160
atccactggc ttttcgtta 19

<210> SEQ ID NO 161
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 161
tcatgatttt aaacttaacc ctgctcctt 29

<210> SEQ ID NO 162
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 162
gcatatgact ctgtttatct tcccttgt 28

<210> SEQ ID NO 163
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 163
ctaagggatg ataaagga 18

<210> SEQ ID NO 164
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 164
ttctaaggga tgataatgga 20

<210> SEQ ID NO 165
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 165
gcatcccgct cccaagaaa 19

<210> SEQ ID NO 166
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 166
caccaagaga ttggatcaaa tgtaattatt attatagttc 40

<210> SEQ ID NO 167
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 167
cagcgtttca tatattttg gat 23

<210> SEQ ID NO 168
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 168
cagcgtttca tatatctttg gat 23

<210> SEQ ID NO 169
<211> LENGTH: 24
<212> TYPE: DNA

<213> ORGANISM: Artificial Sequence
<220> FEATURE:
<223> OTHER INFORMATION: synthetic oligonucleotide

<400> SEQUENCE: 169
tttttgagct aatgggcctt ctct 24

<210> SEQ ID NO 170
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 170
ggtaggtttc gtagggtaaa agct 24

<210> SEQ ID NO 171
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 171
acatctctct cataaac 17

<210> SEQ ID NO 172
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 172
acatctctca cataaac 17

<210> SEQ ID NO 173
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 173
tgattattag ggttttaatg tggtggattg t 31

<210> SEQ ID NO 174
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 174
gcatcaaggt gccttcttta acatg 25

<210> SEQ ID NO 175
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 175
ccctctgttc gactaca 17

<210> SEQ ID NO 176
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 176
atccctctgt ttgactaca 19

<210> SEQ ID NO 177
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 177
atcagagact gagtctgcat atcca 25

<210> SEQ ID NO 178
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 178
tcctcgcatc ttcaaaacta gtgtt 25

<210> SEQ ID NO 179
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 179
ctgtttcaaa cctgaatgt 19

<210> SEQ ID NO 180
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 180
ctgtttcaaa cctaaatgt 19

<210> SEQ ID NO 181
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 181
aagcagtgga ctatggttgg ttaat 25

<210> SEQ ID NO 182
<211> LENGTH: 27
<212> TYPE: DNA
<213> ORGANISM: Artificial Sequence
<220> FEATURE:

<223> OTHER INFORMATION: synthetic oligonucleotide

<400> SEQUENCE: 182
tctcactcaa atggattgtg ttcatgt 27

<210> SEQ ID NO 183
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 183
agccgtaaac taattagag 19

<210> SEQ ID NO 184
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 184
cagccgtaaa ctacttagag 20

<210> SEQ ID NO 185
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 185
ctattcactt tcaataatgg ctacgttgc 29

<210> SEQ ID NO 186
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 186
caggcgagaa gtatgtaaag tcgtt 25

<210> SEQ ID NO 187
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 187
tggcggatct caaatt 16

<210> SEQ ID NO 188
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 188
cgtggcggat ctcatatt 18

<210> SEQ ID NO 189
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 189
tgtttgtttc ttttgtgggt tttgtga 27

<210> SEQ ID NO 190
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 190
tgaaccttga tatcatcgtt gtagacacta taata 35

<210> SEQ ID NO 191
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 191
attttgttgt atgagcttt 19

<210> SEQ ID NO 192
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 192
attttgttgt aggagcttt 19

<210> SEQ ID NO 193
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 193
ggtggctttg aaatttatct tagtaggtct t 31

<210> SEQ ID NO 194
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 194
attgtgaatc ccataacgct taaggt 26

<210> SEQ ID NO 195
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 195
aactctgcaa agctt 15

<210> SEQ ID NO 196
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 196
aactctgcga agctt 15

<210> SEQ ID NO 197
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 197
gctcgatgcc atctcgtcta g 21

<210> SEQ ID NO 198
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 198
ctcttgagca tgtggacact ga 22

<210> SEQ ID NO 199
<211> LENGTH: 12
<212> TYPE: DNA
<213> ORGANISM: Artificial Sequence
<220> FEATURE:
<223> OTHER INFORMATION: synthetic oligonucleotide

<400> SEQUENCE: 199
cggcctggcc cc 12

<210> SEQ ID NO 200
<211> LENGTH: 12
<212> TYPE: DNA
<213> ORGANISM: Artificial Sequence
<220> FEATURE:
<223> OTHER INFORMATION: synthetic oligonucleotide

<400> SEQUENCE: 200
cggcccggcc cc 12

<210> SEQ ID NO 201
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 201
gatgccatct cgtctagtaa gctt 24

<210> SEQ ID NO 202
<211> LENGTH: 21

<212> TYPE: DNA
<213> ORGANISM: Artificial Sequence
<220> FEATURE:
<223> OTHER INFORMATION: synthetic oligonucleotide

<400> SEQUENCE: 202
acttatttta aatcaaaagt g 21

<210> SEQ ID NO 203
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 203
tgtacttatt ttaaatcgaa agtg 24

<210> SEQ ID NO 204
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 204
agttttggca aattaattgg agagtaggt 29

<210> SEQ ID NO 205
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 205
cgaccttatc aatgagagac aaaataatat tagca 35

<210> SEQ ID NO 206
<211> LENGTH: 14
<212> TYPE: DNA
<213> ORGANISM: Artificial Sequence
<220> FEATURE:
<223> OTHER INFORMATION: synthetic oligonucleotide

<400> SEQUENCE: 206
ccaaccaaga aaat 14

<210> SEQ ID NO 207
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 207
atccaaccag gaaaat 16

<210> SEQ ID NO 208
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 208
gtgtccatcg tcatgaagat ctct 24

<210> SEQ ID NO 209
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 209
caagtgccct ttgttgagat tcc 23

<210> SEQ ID NO 210
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 210
acgcaaaaac actctgataa 20

<210> SEQ ID NO 211
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 211
acgcaaaaac actctcataa 20

<210> SEQ ID NO 212
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 212
gtttgaaact gaaaaagagt agtaagcaca t 31

<210> SEQ ID NO 213
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 213
gcaaatcaca tgtagcgttt aaggt 25

<210> SEQ ID NO 214
<211> LENGTH: 13
<212> TYPE: DNA
<213> ORGANISM: Artificial Sequence
<220> FEATURE:
<223> OTHER INFORMATION: synthetic oligonucleotide

<400> SEQUENCE: 214
cgcgactcac gcg 13

<210> SEQ ID NO 215
<211> LENGTH: 13
<212> TYPE: DNA
<213> ORGANISM: Artificial Sequence
<220> FEATURE:
<223> OTHER INFORMATION: synthetic oligonucleotide

<400> SEQUENCE: 215
cgcgacgcac gcg 13

<210> SEQ ID NO 216
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 216
acagaggcgg gaagtgttta ttt 23

<210> SEQ ID NO 217
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 217
tcttcttctt cgttcgtttc ggaaa 25

<210> SEQ ID NO 218
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 218
cagaactgat gagttc 16

<210> SEQ ID NO 219
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 219
cagaactgat gagtcc 16

<210> SEQ ID NO 220
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 220
ggaaaatgca aggaagagca 20

<210> SEQ ID NO 221
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 221
tgaatgatct ctttgctgtg aaa 23

<210> SEQ ID NO 222
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 222
ttgctgtgaa atttttaag 19

<210> SEQ ID NO 223
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 223
ttgctgtgaa attttcaag 19

<210> SEQ ID NO 224
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 224
cacaagcaat ttcaaagaag ca 22

<210> SEQ ID NO 225
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 225
tctccaatga aagaaaagat tgg 23

<210> SEQ ID NO 226
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 226
caagagaaaa gaaagtacta c 21

<210> SEQ ID NO 227
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 227
aagagaaaag aaagaactac 20

<210> SEQ ID NO 228
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 228
ggacgaacag gactcaaaac tctata 26

<210> SEQ ID NO 229
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 229
gcgctaaccc ctttcaaatt cttat 25

<210> SEQ ID NO 230
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 230
tgtattttcc tttgacagta a 21

<210> SEQ ID NO 231
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 231
ctgtattttc ctttcacagt aa 22

<210> SEQ ID NO 232
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 232
ttgatgctac gtatcgaata agaaatgaat agaa 34

<210> SEQ ID NO 233
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 233
atcttggaaa ccctctttgg tgtt 24

<210> SEQ ID NO 234
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 234
accaccaaca aataa 15

<210> SEQ ID NO 235

<211> LENGTH: 14
<212> TYPE: DNA
<213> ORGANISM: Artificial Sequence
<220> FEATURE:
<223> OTHER INFORMATION: synthetic oligonucleotide

<400> SEQUENCE: 235
ccaccagcaa ataa 14

<210> SEQ ID NO 236
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 236
tgaggactga cagaatgcac aag 23

<210> SEQ ID NO 237
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 237
gaggtagtgt acatttgcga cgat 24

<210> SEQ ID NO 238
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 238
atctaagaaa ctttaattaa aa 22

<210> SEQ ID NO 239
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 239
agatctaaga aacttttatt aaaa 24

<210> SEQ ID NO 240
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 240
gcttgtcaat gccttccttg tta 23

<210> SEQ ID NO 241
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 241
cacattgagg tccattgata atattaggat gtta 34

<210> SEQ ID NO 242
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 242
ctagagagta tcaaacatc 19

<210> SEQ ID NO 243
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 243
ctagagagta tgaaacatc 19

<210> SEQ ID NO 244
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 244
attttgtttg tttcgtttga gtcttatcgt 30

<210> SEQ ID NO 245
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 245
ttgacgactt aatgcattca ctgaga 26

<210> SEQ ID NO 246
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 246
caccacgtgt tagtg 15

<210> SEQ ID NO 247
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 247
ccaccacatg ttagtg 16

<210> SEQ ID NO 248
<211> LENGTH: 33
<212> TYPE: DNA

<213> ORGANISM: Artificial Sequence
<220> FEATURE:
<223> OTHER INFORMATION: synthetic oligonucleotide

<400> SEQUENCE: 248
ttaacttttt ttttctttta ttaaccaatc gcg 33

<210> SEQ ID NO 249
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 249
ggcaagtttg gtgagttctt atggt 25

<210> SEQ ID NO 250
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 250
tttaataaat ttgtgggacc c 21

<210> SEQ ID NO 251
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 251
aataaagttg tgggaccc 18

<210> SEQ ID NO 252
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 252
ccaaacttgc ctcttgcaga ag 22

<210> SEQ ID NO 253
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 253
ttagagcatc attaacccca cctttt 26

<210> SEQ ID NO 254
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 254
ctcacaaggt gcataca 17

<210> SEQ ID NO 255
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 255
actcacaagg tgcacaca 18

<210> SEQ ID NO 256
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 256
ctcacaaggt gcactgtttc ac 22

<210> SEQ ID NO 257
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 257
ggcttccagt ccacaattat tcca 24

<210> SEQ ID NO 258
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 258
catagtagtc cacatgagta t 21

<210> SEQ ID NO 259
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 259
catagtagtc cacgtgagta t 21

<210> SEQ ID NO 260
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 260
accttaatca gtagactata gcgcttct 28

<210> SEQ ID NO 261
<211> LENGTH: 27
<212> TYPE: DNA
<213> ORGANISM: Artificial Sequence
<220> FEATURE:

<223> OTHER INFORMATION: synthetic oligonucleotide

<400> SEQUENCE: 261
ggttgctcaa tatcgagact ttcttct 27

<210> SEQ ID NO 262
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 262
ttttcaaagt acccctaatc 20

<210> SEQ ID NO 263
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 263
tttcaaagta cgcctaatc 19

<210> SEQ ID NO 264
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 264
gttgtgcact aatgcatctc acatt 25

<210> SEQ ID NO 265
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 265
atgttcatgt attgctctgc tttagtct 28

<210> SEQ ID NO 266
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 266
cagtggatgc tatgcg 16

<210> SEQ ID NO 267
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 267
tcagtggatg ttatgcg 17

<210> SEQ ID NO 268
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 268
ttgtatccac caaatggcat cca 23

<210> SEQ ID NO 269
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 269
aatagagaag ttgggcaagt aaaagagatt 30

<210> SEQ ID NO 270
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 270
cttgaccaaa ccttatg 17

<210> SEQ ID NO 271
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 271
cttgaccaaa ctttatg 17

<210> SEQ ID NO 272
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 272
ttttcatgtc aatattcccc ctcaagt 27

<210> SEQ ID NO 273
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 273
gagggatgtc ttcatggttt ccaa 24

<210> SEQ ID NO 274
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 274
ttcgtcctag caacca 16

<210> SEQ ID NO 275
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 275
ttcgtcctag cgacca 16

<210> SEQ ID NO 276
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 276
ttttcattca aaagatcaaa atca 24

<210> SEQ ID NO 277
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 277
caacgtgaaa tgcaggtga 19

<210> SEQ ID NO 278
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 278
cctctttcac cattata 17

<210> SEQ ID NO 279
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 279
ctctttcacc agtatat 17

<210> SEQ ID NO 280
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 280
ccggatggaa cagttctttg 20

<210> SEQ ID NO 281
<211> LENGTH: 28

<212> TYPE: DNA
<213> ORGANISM: Artificial Sequence
<220> FEATURE:
<223> OTHER INFORMATION: synthetic oligonucleotide

<400> SEQUENCE: 281
ggaatcaatt acatcacaac tttatcag 28

<210> SEQ ID NO 282
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 282
tagctccaat tggtttt 17

<210> SEQ ID NO 283
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 283
tagctccagt tggtttt 17

<210> SEQ ID NO 284
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 284
gaggagcacg gaacaagatt 20

<210> SEQ ID NO 285
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 285
acttggtcgg cccaaacta 19

<210> SEQ ID NO 286
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 286
aatttttgaa tatcaatttt 20

<210> SEQ ID NO 287
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 287
tgaaattttt gaatattaat ttt 23

<210> SEQ ID NO 288
<211> LENGTH: 38
<212> TYPE: DNA
<213> ORGANISM: Artificial Sequence
<220> FEATURE:
<223> OTHER INFORMATION: synthetic oligonucleotide

<400> SEQUENCE: 288
cctagggtat caatttttag tttttttac taaatggt 38

<210> SEQ ID NO 289
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 289
ctcgcaaata attttcttaa gtttttgtta ccaaa 35

<210> SEQ ID NO 290
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 290
accattcgcg ttttg 15

<210> SEQ ID NO 291
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 291
accattcggg ttttg 15

<210> SEQ ID NO 292
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 292
tttttcgggt ttggaaatat agga 24

<210> SEQ ID NO 293
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 293
acccgaaaac caaaccaaaa cc 22

<210> SEQ ID NO 294
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 294
ccgatttcgg tcttagtt 18

<210> SEQ ID NO 295
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 295
tccgatttcg gttttagtt 19

<210> SEQ ID NO 296
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 296
gggtttggaa atataggaac cattcg 26

<210> SEQ ID NO 297
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 297
acccgaaaac caaaccaaaa cc 22

<210> SEQ ID NO 298
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 298
aaccaaaacc aaaccga 17

<210> SEQ ID NO 299
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 299
aaaccaaaac cgaaccga 18

<210> SEQ ID NO 300
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 300
tttaatctag aatctcgttt agttctgggc 30

<210> SEQ ID NO 301
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 301
cttgacaaaa tataaggtt 19

<210> SEQ ID NO 302
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 302
cttgacaaag tataaggtt 19

<210> SEQ ID NO 303
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 303
catgcaatct tccaaactta aaaat 25

<210> SEQ ID NO 304
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 304
gttattcttt attatctatg gttttatctt ttg 33

<210> SEQ ID NO 305
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 305
cacaaaccga accaa 15

<210> SEQ ID NO 306
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 306
ttacacaaac caaaccaa 18

<210> SEQ ID NO 307
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 307
aattggactc aaaattatct taaatattag ttggt 35

<210> SEQ ID NO 308
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 308
gggtataggt tcggttttat ttgttctaga 30

<210> SEQ ID NO 309
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 309
caaataccga aataac 16

<210> SEQ ID NO 310
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 310
ccaaatacca aaataac 17

<210> SEQ ID NO 311
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 311
ggtaacatgt attcatc 17

<210> SEQ ID NO 312
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 312
ggtaacatgt cttcatc 17

<210> SEQ ID NO 313
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 313
tttgtagttg aacaaagttg aagga 25

<210> SEQ ID NO 314

<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 314
agggtacgtt ggaagggtct 20

<210> SEQ ID NO 315
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 315
gtaacgcaga tttgt 15

<210> SEQ ID NO 316
<211> LENGTH: 14
<212> TYPE: DNA
<213> ORGANISM: Artificial Sequence
<220> FEATURE:
<223> OTHER INFORMATION: synthetic oligonucleotide

<400> SEQUENCE: 316
gtaacgcgga tttg 14

<210> SEQ ID NO 317
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 317
cggcactaga atacgattcc tc 22

<210> SEQ ID NO 318
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 318
aaatgtgact taaacaagct acctctt 27

<210> SEQ ID NO 319
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 319
gtttgacgta aagaaa 16

<210> SEQ ID NO 320
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 320
gtttgacgga aagaa 15

<210> SEQ ID NO 321
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 321
ggaggaagag atcggtgatg 20

<210> SEQ ID NO 322
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 322
tggtagatga aacatccaag ca 22

<210> SEQ ID NO 323
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 323
gatcactcag ttaaat 16

<210> SEQ ID NO 324
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 324
gatcactcgg ttaaa 15

<210> SEQ ID NO 325
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 325
tggcaattcc ccataaataa a 21

<210> SEQ ID NO 326
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 326
tgttcatggt tttgaaagtg aaa 23

<210> SEQ ID NO 327
<211> LENGTH: 17
<212> TYPE: DNA

-continued

```
<213> ORGANISM: Artificial Sequence
<220> FEATURE:
<223> OTHER INFORMATION: synthetic oligonucleotide

<400> SEQUENCE: 327

tactagaatg caacctt                                                  17


<210> SEQ ID NO 328
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 328

tactagtatg caacctt                                                  17


<210> SEQ ID NO 329
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 329

tcagattcca ggatcgaggt                                               20


<210> SEQ ID NO 330
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 330

gctccactcg aaatcgtcac                                               20
```

CLUBROOT RESISTANCE IN *Brassica*

CROSS-REFERENCE TO RELATED APPLICATION

This Application is a national stage of International Patent Application No. PCT/US2022/013522, filed Jan. 24, 2022, which claims the benefit of U.S. Provisional Application 63/142,717, filed on Jan. 28, 2021, each of the foregoing is hereby incorporated by reference herein in its entirety.

REFERENCE TO SEQUENCE LISTING SUBMITTED ELECTRONICALLY

The official copy of the sequence listing is submitted electronically via EFS-Web as an ASCII formatted sequence listing with a file named 8541-WO-PCT_ST25, created on Jan. 19, 2022 and having a size of 65 kilobytes, which is filed concurrently with the specification. The sequence listing comprised in this ASCII formatted document is part of the specification and is herein incorporated by reference in its entirety.

FIELD OF THE DISCLOSURE

The present disclosure relates to plants resistant to diseases, in particular to *Brassica* plants resistant to clubroot disease.

BACKGROUND

Clubroot is a widespread disease that causes major economic losses and has emerged as serious threat in many *Brassica* growing areas globally and particularly in North America. Clubroot disease is caused by *Plasmodiophora brassicae*, a soil-borne, root-infecting protist pathogen and phylogenetical intermediate between a fungus and bacteria. *P. brassicae* infection leads to swollen roots or 'galls' that hijack the host water and nutrient supplies, causing wilting, death and loss of yield. Management of clubroot is challenging because of two unique attributes of *P. brassicae*. The organism has very short life cycles and can produce multiple generations within a season. Second, each infected gall produces billions of spores that can survive in soil for many years and, in some cases, more than 15 years. Local spread of spores can be facilitated by wet conditions, but most dispersal of the pathogen is caused by transportation of infested soil or compost, e.g., on tools, equipment or plant material. *P. brassicae* has a wide host range in the *Brassica* family including numerous weed species.

There are currently no effective fungicides for the widespread control of clubroot. In the absence of effective chemical control options, developing sources of genetic resistance has the most potential for protecting *Brassica* from clubroot. Clubroot resistance, mostly qualitative and race-specific, exists in some *Brassica* vegetables such as rutabaga, turnips, and cabbages. including in Chinese cabbage (Yoshikawa. 1983. Japan Agricultural Research Quarterly, 17:6-11). Chinese cabbage F1 hybrids with this resistance have been shown to have good protection against clubroot, although a small number of races have been able to break through this resistance. To date, more than 10 loci have been identified that contribute to clubroot resistance, these include: CRa, CRb, CRc, CRk (Matsumoto et al. 1998. *J Jpn Soc Hortic Sci* 74:367-373; Piao et al. 2004. *Theor Appl Genet* 108:1458-1465; Sakamoto et al. 2008. *Theo Appl Genet* 117:759-767), Crr1, Crr2, Crr3, Crr4 (Suwabe et al. 2003. *Theo Appl Genet* 107:997-1002; Suwabe et al. 2006. *Genetics* 173:309-319; Hirai et al. 2004. *Theor Appl Genet* 108:639-643), CRd (Pang et al. 2018. *Front Plant Sci* 9:822), PbBa3.1, PbBa3.2, PbBa3.3, PbBa1.1, PbBa8.1 (Chen et al. 2013. *PLOS ONE* 8(12):e85307), Rcr1 (Chu et al. 2014. *BMC Genomics* 15(1): 1166), Rcr4, Rcr8, and Rcr9 (Yu et al. 2017. *Sci Rep* 7(1): 4516).

Nonetheless different subgroups or races of clubroot pathogen have been identified that exhibit virulence against plants having loci associated with a particular clubroot resistance. Additionally, repeated plantings of *Brassica* plants having the same (single or multiple) clubroot resistance loci may lead to the diminution and/or complete loss of effectiveness due to selection pressure for pathogens that overcome these genetic sources of resistance. This is of particular concern when varieties with clubroot resistant loci are challenged by high pathogen loads, which increases the probability for evolving new races that are virulent even for plants having those loci. Therefore, in order to mitigate the problem of evolving pathogen resistance and to protect against a broader spectrum of pathogens, there is a need and desire to identify, introgress, and track new sources of clubroot resistance in *Brassica* species, particularly for the commercially significant species such as *Brassica napus.*

SUMMARY OF THE DISCLOSURE

Disclosed herein are genetic marker alleles, methods, and assays for identifying and tracking clubroot resistance loci on *Brassica* chromosome N8. The markers, methods, and assays are based, at least in part, on discoveries generated by an extensive and intensive genetic screening effort to identify new markers and/or sources of clubroot disease. The disclosed markers are tightly linked to the resistance loci CrB8, CrG8, CrE8, CrM8, and CrI8 described herein. The disclosed markers appear to be uniquely specific to resistant donor lines disclosed herein and/or are so rare in publicly available germplasm that they have not been previously identified as being linked to clubroot resistance.

The disclosed CrB8, CrG8, CrE8, CrM8, and CrI8 markers are suitable for high-throughput marker assisted selection. In certain examples, the markers are particularly suited for the identification of loci that are rare or particularly unusual. Additionally, the disclosed markers are suitable for the identification and introgression of clubroot resistance in inbred germplasm for each loci on chromosome N8 and can be used to generate hybrid clubroot resistant *Brassica* plants and seed.

Provided is a method of identifying a *Brassica* plant, cell, or germplasm comprising a clubroot disease resistance locus by obtaining a sample of nucleic acid from a *Brassica* plant, cell, or germplasm and screening the sample for a molecular marker allele, or a haplotype of molecular marker alleles, linked to one or more of the following clubroot resistance loci: (1) CrB8 located on chromosome N8 interval flanked by and including 12.94 cM and 16.44 cM, (2) CrG8 located on chromosome N8 interval flanked by and including 13.94 cM and 14.07 cM, (3) CrE8 located on chromosome N8 interval flanked by and including 12.87 cM and 13.98 cM, (4) CrM8 located on chromosome N8 interval flanked by and including 13.2 cM and 13.38 cM, or (5) CrI8 located on chromosome N8 interval flanked by and including 13.2 cM and 13.7 cM. As disclosed herein, the CrB8 locus corresponds to physical position 10,656,081 to position 13,303,318 of chromosome 8 (Chr 8); the CrG8 locus corresponds to physical position 11,124,294 to position 11,338,475 of Chr 8; the CrE8 locus corresponds to the physical position 10,146,787 to position 11,793,943 of Chr 8; the CrM8 locus corresponds to position 10,959,267 to position 11,159,261 of Chr 8; and the CrI8 locus corresponds to position 10,986,309 to position 11,191,524 on Chr 8 of a *B. napus* reference genome. Examples of single nucleotide polymorphism (SNP) markers that correspond to resistance (RES) and susceptibility (SUS) alleles for clubroot disease are identified in Tables 1-8. The probe sequences disclosed in Tables 1-8 comprises sequence flanking each of these SNPs. Many of the probe sequences (including the bolded and underlined SNP nucleotide) displayed in Tables 1-8 correspond to the genomic strand sequence complementary to that shown in the columns for the corresponding RES and SUS alleles. Thus for every method disclosed herein for a particular SNP nucleotide or flanking maker sequence, it is understood that the disclosed method also includes the SNP nucleotide or flanking sequence, respectively, on the complementary strand.

In some examples, the method of identifying a *Brassica* plant, cell, or germplasm comprising a clubroot disease resistance locus comprises screening for at least one of the following molecular marker alleles (e.g., a haplotype that includes two or more of the following marker alleles): a CrB8 resistance marker allele identified in Table 1 or Table 2 herein; a CrG8 resistance marker allele identified in Table 3 herein; a CrE8 resistance marker allele identified in Table 4 or Table 5 herein; a CrM8 resistance marker allele identified in Table 6 or Table 7 herein; or a CrI8 resistance marker allele identified in Table 8 herein. Thus, for example, the method can include screening for a haplotype comprising (A) 2, 3, 4, 5, 6 or more resistance marker alleles in Table 1 or Table 2 herein; (B) 2, 3, 4, 5, 6 or more resistance marker alleles in Table 3 herein; (C) 2, 3, 4, 5, 6 or more resistance marker alleles identified in Table 4 or Table 5 herein; (D) 2, 3, 4, 5, 6 or more resistance marker alleles in Table 6 or Table 7 herein; or (E) 2, 3, 4, 5, 6 or more marker resistance alleles in Table 8 herein.

Additionally, the disclosed method can include screening for one or more CrB8 resistance alleles identified in Table 1 or Table 2 herein in combination with one or more CrG8 resistance allele identified in Table 3 herein, one or more CrE8 resistance allele identified in Table 4 or Table 5 herein, one or more CrM8 alleles identified in Table 6 or Table 7 herein, or one or more CrI8 resistance alleles identified in Table 8 herein. Or the method can include screening for one or more CrG8 resistance allele identified in Table 3 herein in combination with one or more CrB8 resistance alleles identified in Table 1 or Table 2 herein, one or more CrE8 resistance allele identified in Table 4 or Table 5 herein, one or more CrM8 alleles identified in Table 6 or Table 7 herein, or one or more CrI8 resistance alleles identified in Table 8 herein. Or the method can include screening for one or more CrE8 resistance allele identified in Table 4 or Table 5 herein in combination with one or more CrB8 resistance alleles identified in Table 1 or Table 2 herein, one or more CrG8 resistance allele identified in Table 3 herein, one or more CrE8 resistance allele identified in Table 4 or Table 5 herein, one or more CrM8 alleles identified in Table 6 or Table 7 herein, or one or more CrI8 resistance alleles identified in Table 8 herein. Or the method can include screening for one or more CrM8 alleles identified in Table 6 or Table 7 herein in combination with one or more CrB8 resistance alleles identified in Table 1 or Table 2 herein, one or more CrG8 resistance allele identified in Table 3 herein, one or more CrE8 resistance allele identified in Table 4 or Table 5 herein, or one or more CrI8 resistance alleles identified in Table 8 herein. Or the method can include screening for one or more CrI8 resistance alleles identified in Table 8 herein in combination with one or more CrB8 resistance alleles identified in Table 1 or Table 2 herein, one or more CrG8 resistance allele identified in Table 3 herein, one or more CrE8 resistance allele identified in Table 4 or Table 5 herein, or one or more CrM8 alleles identified in Table 6 or Table 7 herein.

In some examples, the method of identifying a *Brassica* plant, cell, or germplasm comprising a clubroot disease resistance locus comprises screening for at least one of the following resistance marker alleles: (1) N101BW0-001-Q001 (SEQ ID NO:23), N101T3M-001-Q001 (SEQ ID NO:30), N101T3P-001-Q001 (SEQ ID NO:33), or N101T3R-001-Q001 (SEQ ID NO:37) allele linked to CrB8; (2) N100C6A-001-Q001 (SEQ ID NO:44) allele linked to CrG8; (3) N100CJT-001-Q001 (SEQ ID NO:180), N101T3T-001-Q001 (SEQ ID NO:219), or N101T3U-001-Q001 (SEQ ID NO:222) allele linked to CrE8; (4) N100CDD-001-Q001 (SEQ ID NO: 262), N101T3X-001-Q001 (SEQ ID NO:275), N101T3Y-001-Q001 (SEQ ID NO:278), or N101T41-001-Q001 (SEQ ID NO:282) allele linked to CrM8; (5) N101T0T-001-Q003 (SEQ ID NO:302) allele linked to CrI8.

Moreover, each of the methods for identifying a *Brassica* plant, cell, or germplasm comprising a clubroot disease resistance locus disclosed herein can further include selecting the *Brassica* plant, cell, or germplasm thereof based on the presence of the molecular marker allele or a haplotype of molecular marker alleles linked to the clubroot resistance locus. Thus, provided herein is a method of selecting a plant identified by any of the methods disclosed herein as having one or more CrB8 resistance allele identified in Table 1 or Table 2 herein; one or more CrG8 resistance allele identified in Table 3 herein; one or more CrE8 resistance allele identified in Table 4 or Table 5 herein; one or more CrM8 allele identified in Table 6 or Table 7 herein; or one or more CrI8 resistance allele identified in Table 8 herein. The disclosed selection methods are particularly useful for identifying and selecting such a *Brassica* plant, cell, or germplasm from a plurality (e.g., in a breeding population). Accordingly the disclosed methods can be used for marker assisted selection and/or introgression of the CrB8, CrG8, CrE8, CrM8, and CrI8 loci disclosed herein.

For example, disclosed herein is a method of introducing (e.g., introgressing) at least one clubroot resistance locus into a *Brassica* plant by crossing a first parent *Brassica* plant comprising at least one clubroot resistance locus with a second *Brassica* plant to produce progeny plants, which can be screened for the presence or absence of one or more CrB8, CrG8, CrE8, CrM8, or CrI8 clubroot disease resistance locus using any of the screening methods disclosed herein. Thus progeny plants having at least one molecular marker allele or a haplotype that includes two or more of marker alleles identified in Tables 1-8 can be identified using any of the marker allele screening methods disclosed herein (optionally, such method can include screening for the presence of one or more susceptibility alleles disclosed in Tables 1-8 that corresponds to the one or more screened—for resistance alleles and removing or discarding plants having the susceptibility allele instead of the screened—for resistance allele). The introgression method can then include selecting one or more progeny plants having the CrB8, CrG8, CrE8, CrM8, or CrI8 clubroot disease resistance locus that is screened for. In particular examples, the introgression method can further include crossing the selected one or more progeny plants with the second parent *Brassica* plant to produce backcross progeny plants. Such backcross progeny plants can be screened for the presence or absence of the CrB8, CrG8, CrE8, CrM8, or CrI8 clubroot disease resistance marker alleles to thereby identify and select backcross progeny plants having a CrB8, CrG8, CrE8, CrM8, or CrI8 clubroot disease resistance locus. The selected backcross progeny plant can itself be backcrossed to the second parent *Brassica* plant to produce further backcross progeny plants, which can be screened as described to enable selection of further backcross progeny plants having a CrB8, CrG8, CrE8, CrM8, or CrI8 clubroot disease resistance locus. Such backcrossing, screening, and selection can be repeated for two, three, four, five, six or more generations to introgress the CrB8, CrG8, CrE8, CrM8, or CrI8 clubroot disease resistance locus into the genetic background of the second parent *Brassica* plant.

The disclosure can be more fully understood from the following detailed description and the accompanying drawings and Sequence Listing, which form a part of this application. The sequence descriptions and sequence listing attached hereto comply with the rules governing nucleotide and amino acid sequence disclosures in patent applications as set forth in 37 C.F.R. §§ 1.821 and 1.825. The sequence descriptions comprise the three letter codes for amino acids as defined in 37 C.F.R. §§ 1.821 and 1.825, which are incorporated herein by reference. When one strand of each nucleic acid sequence is shown, the complementary strand is understood to be included by any reference to the displayed strand.

DETAILED DESCRIPTION

Terms used in the claims and specification are defined as set forth below unless otherwise specified. It must be noted that, as used in the specification and the appended claims, the singular forms "a," "an" and "the" include plural referents unless the context clearly dictates otherwise.

Terms and Definitions

An "allele" is one of several alternative forms of a gene occupying a given locus on a chromosome. When all the alleles present at a given locus on a chromosome are the same, that plant is "homozygous" at that locus. If the alleles present at a given locus on a chromosome differ, that plant is "heterozygous" at that locus.

An "amplicon" is amplified nucleic acid, e.g., a nucleic acid that is produced by amplifying a template nucleic acid by any available amplification method (e.g., polymerase chine reaction (PCR), ligase chain reaction (LCR), transcription, or the like).

"Backcrossing" refers to the process whereby hybrid progeny plants are repeatedly crossed back to one of the parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. Backcrossing has been widely used to introduce new traits into plants. See e.g., Jensen, N., Ed. *Plant Breeding Methodology*, John Wiley & Sons, Inc., 1988. In a typical backcross protocol, the original variety of interest (recurrent parent) is crossed to a second variety (nonrecurrent parent) that carries a gene of interest to be transferred. The resulting progeny from this cross are then crossed again to the recurrent parent, and the process is repeated until a plant is obtained wherein essentially all of the desired morphological and physiological characteristics of the recurrent plant are recovered in the converted plant, in addition to the transferred gene from the nonrecurrent parent.

"*Brassica*" refers to any one of *Brassica napus* (AACC, 2n=38), *Brassica juncea* (AABB, 2n=36), *Brassica carinata* (BBCC, 2n=34), *Brassica rapa* (syn. *B. campestris*) (AA, 2n=20), *Brassica oleracea* (CC, 2n=18) or *Brassica nigra* (BB, 2n=16).

The term "cross" (or "crossed") refers to the fusion of gametes via pollination to produce progeny (e.g., cells, seeds, and plants). This term encompasses both sexual crosses (i.e., the pollination of one plant by another) and selfing (i.e., self-pollination, for example, using pollen and ovule from the same plant).

The term "elite line" means any line that has resulted from breeding and selection for superior agronomic performance. An elite plant is any plant from an elite line.

The term "gene" (or "genetic element") may refer to a heritable genomic DNA sequence with functional significance. A gene includes a nucleic acid fragment that expresses a functional molecule such as, but not limited to, a specific protein, including regulatory sequences preceding (5' non-coding sequences) and following (3' non-coding sequences) the coding sequence, as well as intervening intron sequences. The term "gene" may also be used to refer to, for example and without limitation, a cDNA and/or an mRNA encoded by a heritable genomic DNA sequence.

The term "genome" as it applies to a prokaryotic and eukaryotic cell or organism cells encompasses not only chromosomal DNA found within the nucleus, but organelle DNA found within subcellular components (e.g., mitochondria, or plastid) of the cell.

A "genomic sequence" or "genomic region" is a segment of a chromosome in the genome of a cell that is present on either side of the target site or, alternatively, also comprises the target site or a portion thereof. An "endogenous genomic sequence" refers to genomic sequence within a plant cell.

As used herein, "gene" includes a nucleic acid fragment or sequence that expresses a functional molecule such as, but not limited to, a specific protein coding sequence and regulatory elements, such as those preceding (5' non-coding sequences) and following (3' non-coding sequences) the coding sequence.

A "genomic locus" as used herein refers to the genetic or physical location on a chromosome of a gene.

The term "genotype" refers to the physical components, i.e., the actual nucleic acid sequence at one or more loci in an individual plant.

The term "germplasm" refers to genetic material of or from an individual plant or group of plants (e.g., a plant line, variety, and family), or a clone derived from a plant or group of plants. A germplasm may be part of an organism or cell, or it may be separate (e.g., isolated) from the organism or cell. In general, germplasm provides genetic material with a specific molecular makeup that is the basis for hereditary qualities of the plant. As used herein, "germplasm" refers to cells of a specific plant; seed; tissue of the specific plant (e.g., tissue from which new plants may be grown); and non-seed parts of the specific plant (e.g., leaf, stem, pollen, and cells). Thus, "germplasm" is used herein synonymously with "genetic material" and may be used to refer to seed (or other plant material) from which a plant may be propagated. A "germplasm bank" may refer to an organized collection of different seed or other genetic material (wherein each genotype is uniquely identified) from which a known cultivar may be cultivated, and from which a new cultivar may be generated. In embodiments, a germplasm utilized in a method or plant as described herein is from a canola line or variety. In particular examples, a germplasm is seed of the canola line or variety. In particular examples, a germplasm is a nucleic acid sample from the *Brassica* line or variety.

A "haplotype" is the genotype of an individual at a plurality of genetic loci, i.e. a combination of alleles. Typically, the genetic loci described by a haplotype are physically and genetically linked, i.e., on the same chromosome segment.

The terms "increased" or "improved" in connection with "clubroot resistance" is used herein to refer to plants having increased growth, productivity, and/or reduction in root size or number of root nodules, relative a plant that is susceptible (lacking resistance) to clubroot disease, when grown in a field comprising *Plasmodiophora brassicae*.

The term "introgression" refers to the transmission of an allele at a genetic locus into a genetic background. For example, introgression of a specific allele can involve a sexual cross between two parents of the same species, where at least one of the parents has the specific allele in its genome, to thereby transfer the allele to at least one progeny. Progeny comprising the specific allele form may be repeatedly backcrossed to a line having a desired genetic background. Backcross progeny may be selected for the specific allele form, so as to produce a new variety wherein the specific allele form has been fixed in the progeny's genetic background. In some embodiments, introgression of a specific allele may occur by recombination between two donor genomes (e.g., in a fused protoplast), where at least one of the donor genomes has the specific allele in its genome. Introgression may involve transmission of a specific allele that may be, for example, a selected allele form of a marker allele, a QTL, and/or a transgene.

As used herein an "isolated" biological component (such as a nucleic acid or protein) has been substantially separated, produced apart from, or purified away from other biological components in the cell of the organism in which the component naturally occurs (i.e., other chromosomal and extra-chromosomal DNA and RNA, and proteins), while effecting a chemical or functional change in the component. For example and without limitation, a nucleic acid may be isolated from a chromosome by breaking chemical bonds connecting the nucleic acid to the remaining DNA in the chromosome and/or the other material previously associated with the nucleic acid in its cellular milieu (e.g., the nucleus). Nucleic acid molecules and proteins that have been "isolated" include nucleic acid molecules and proteins that are enriched or purified. The term also embraces nucleic acids and proteins prepared by recombinant expression in a host cell, as well as chemically-synthesized nucleic acid molecules, proteins, and peptides.

"Marker-assisted selection" (MAS) is a process by which phenotypes are selected based on marker genotypes. Marker assisted selection can include the use of genetic markers to identify plants for inclusion in and/or removal from a breeding program or planting. A molecular marker allele that demonstrates linkage disequilibrium with a desired phenotypic trait (e.g., a QTL) provides a useful tool for the selection of the desired trait in a plant population. Components for implementing a MAS approach include the creation of a dense (information rich) genetic map of molecular markers in the plant germplasm; the detection of at least one QTL based on statistical associations between marker and phenotypic variability; the definition of a set of particular useful marker alleles based on the results of the QTL analysis; and the use and/or extrapolation of this information to the current set of breeding germplasm to enable marker-based selection decisions to be made.

The closer a particular marker is to a gene that encodes a polypeptide that contributes to a particular phenotype (whether measured in terms of genetic or physical distance), the more tightly-linked is the particular marker to the phenotype. In view of the foregoing, it will be appreciated that the closer (whether measured in terms of genetic or physical distance) that a marker is linked to a particular gene, the more likely the marker is to segregate with that gene (e.g., a clubroot disease resistance marker disclosed herein) and its associated phenotype (e.g., clubroot disease resistance disclosed herein). Thus, the tightly linked genetic markers for clubroot resistance disclosed herein can be used in MAS programs to identity *Brassica* varieties that have or can generate progeny that have increased clubroot resistance (relative to parental varieties and/or otherwise isogenic plants lacking that clubroot disease resistance marker), to identify individual plants comprising this clubroot disease resistance trait, and to breed this trait into other *Brassica* varieties to improve their clubroot disease resistance. Marker-assisted selection is discussed in more detail in a subsection hereinbelow.

A "marker set" or a "set" of markers or probes refers to a specific collection of markers (or data derived therefrom) that may be used to identify individuals comprising a trait of interest. Thus, a set of markers linked to clubroot resistance may be used to identify a *Brassica* plant comprising one the clubroot disease resistance loci disclosed herein. Data corresponding to a marker set (or data derived from the use of such markers) may be stored in an electronic medium. While each marker in a marker set is useful in the identification of individuals comprising a trait of interest, subsets of markers in a set (i.e., some but not necessarily all of the markers in a marker set) can be used to effectively identify individuals comprising the trait of interest disclosed herein, i.e., one of the clubroot disease resistance loci disclosed herein.

A "modified gene" is a gene that has been mutated or altered through human intervention. Such a "modified" gene has a sequence that differs from the sequence of the corresponding non-modified gene by at least one nucleotide addition, deletion, or substitution. A "modified" plant is a plant comprising a modified gene or deletion.

As used herein the term "native gene" refers to a gene as it is found in its natural endogenous location operably linked to its own regulatory sequences, which have not been altered by human intervention. In the context of this disclosure, a "modified" gene is not a native gene.

As used herein, a 'nucleic acid molecule" is a polymeric form of nucleotides, which can include both sense and anti-sense strands of RNA, cDNA, genomic DNA, recombinant and synthetic forms and mixed polymers of the above. A nucleotide refers to a ribonucleotide, deoxynucleotide, or a modified form of either type of nucleotide. As used herein "nucleic acid molecule" is synonymous with the terms "nucleic acid", "nucleotide sequence", "nucleic acid sequence", and "polynucleotide." The term includes single- and double-stranded forms of DNA or RNA. A nucleic acid molecule can refer to either or both naturally occurring and modified nucleotides linked together by naturally occurring and/or non-naturally occurring nucleotide linkages. Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications, such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., peptides), intercalators (e.g., acridine, psoralen, etc.), chelators, alkylators, and modified linkages (e.g., alpha anomeric nucleic acids, etc.). The term "nucleic acid molecule" also includes any topological conformation, including single-stranded, double stranded, partially duplexed, triplexed, hairpinned, circular, and padlocked conformations. An "endogenous nucleic acid sequence" refers to a nucleic acid sequence within a plant cell, (e.g. an endogenous allele of a native gene present within the genome of a *Brassica* plant cell).

The term "single-nucleotide polymorphism" (SNP) refers to a DNA sequence variation occurring when a single nucleotide in the genome (or other shared sequence) differs between members of a species or paired chromosomes in an individual. In some examples, markers linked to a clubroot disease resistance locus disclosed herein are SNP markers. Recent high-throughput genotyping technologies such as GoldenGate® and INFINIUM® assays (Illumina, San Diego, CA) may be used in accurate and quick genotyping methods by multiplexing SNPs from 384-plex to >100,000-plex assays per sample.

As used herein, "phenotype" means the detectable characteristics (e.g. clubroot disease resistance) of a cell or organism which can be influenced by genotype.

As used herein, the term "plant material" refers to any processed or unprocessed material derived, in whole or in part, from a plant. For example, and without limitation, a plant material may be a plant part, a seed, a fruit, a leaf, a root, a plant tissue, a plant tissue culture, a plant explant, or a plant cell.

As used herein, the term "plant" may refer to a whole plant, a cell or tissue culture derived from a plant, and/or any part of any of the foregoing. Thus, the term "plant" encompasses, for example and without limitation, whole plants; plant components and/or organs (e.g., leaves, stems, and roots); plant tissue; seed; and a plant cell. A plant cell may be, for example and without limitation, a cell in and/or of a plant, a cell isolated from a plant, and a cell obtained through culturing of a cell isolated from a plant. Thus, the term *Brassica* "plant" may refer to, for example and without limitation, a whole *Brassica* plant; multiple *Brassica* plants; *Brassica* plant cell(s); *Brassica* plant protoplast; *Brassica* tissue culture (e.g., from which a *Brassica* plant can be regenerated); *Brassica* plant callus; *Brassica* plant parts (e.g., seed, flower, cotyledon, leaf, stem, bud, root, and root tip); and *Brassica* plant cells that are intact in a *Brassica* plant or in a part of a *Brassica* plant.

As used herein, a plant or *Brassica* "line" refers to a group of plants that display little genetic variation (e.g., no genetic variation) between individuals for at least one trait. Inbred lines may be created by several generations of self-pollination and selection or, alternatively, by vegetative propagation from a single parent using tissue or cell culture techniques. As used herein, the terms "cultivar," "variety," and "type" are synonymous, and these terms refer to a line that is used for commercial production.

Trait or phenotype: The terms "trait" and "phenotype" are used interchangeably herein. For the purposes of the present disclosure, traits of particular interest are the clubroot disease resistance traits associated with each of the clubroot disease resistance loci disclosed herein.

A "variety" or "cultivar" is a plant line that can be used for commercial production and which is distinct and uniform in its characteristics when propagated. In the case of a hybrid variety or cultivar, the parental lines are distinct, stable, and uniform in their characteristics.

Detection of Disclosed Markers. Each of the markers for the CrB8, CrG8, CrE8, CrM8, and CrI8 loci disclosed herein can be detected by any suitable method for detecting genetic polymorphisms. Suitable methods of detection include nucleotide amplification and/or sequencing of the genetic material, e.g., nucleic acid or genomic DNA sequencing that reveals the presence for a disease resistance marker allele disclosed herein for the CrB8, CrG8, CrE8, CrM8, and CrI8 loci. See Table 1, Table 2, Table 3, Table 4, Table 5, Table 6, Table 7, and Table 8 (Tables 1-8) disclosing clubroot disease resistance markers alleles for each of the loci disclosed herein.

The clubroot disease resistance marker alleles can be identified and distinguished from susceptible allele using allele-specific amplification and PCR-based amplification assays such as TaqMan, rhAmp-SNP, KASPar, and molecular beacons. Such an assay can include the use of one or more probes that detect the marker allele in (i) nucleic acid that is isolated from a plant or (ii) an amplicon that is selectively amplified by amplification of nucleic acid isolated from a plant. Optionally, such an assay can further include an additional set of primers and/or one or more probes that detect the presence of a clubroot susceptible (e.g., wildtype) allele and thereby determine the zygosity (or even the absence) of clubroot resistance loci disclosed herein.

Additional methods for genotyping and detecting a resistant marker allele for the CrB8, CrG8, CrE8, CrM8, and CrI8 loci disclosed herein (or a linked marker) include but are not limited to, hybridization, primer extension, oligonucleotide ligation, nuclease cleavage, minisequencing and coded spheres. Such methods are reviewed in publications including Gut, 2001, *Hum. Mutat.* 17:475; Shi, 2001, *Clin. Chem.* 47:164; Kwok, 2000, *Pharmacogenomics* 1:95; Bhattramakki and Rafalski, "Discovery and application of single nucleotide polymorphism markers in plants", in PLANT GENOTYPING: THE DNA FINGERPRINTING OF PLANTS (CABI Publishing, Wallingford 2001). A wide range of commercially available technologies utilize these and other methods to interrogate the allele disclosed herein (or a linked marker), including Masscode™ (Qiagen, Germantown, Md.), Invader® (Hologic, Madison, Wis.), SnapShot® (Applied Biosystems, Foster City, Calif.), Taqman® (Applied Biosystems, Foster City, Calif.) and Infinium Bead Chip™ and GoldenGate™ allele-specific extension PCR-based assay (Illumina, San Diego, Calif.).

In particular example, detecting a disclosed maker can include nucleic acid sequencing, nucleic acid amplification, or the combined amplification and nucleic acid sequencing of the marker allele and 5 bp or more, 10 bp or more, 15 bp or more, 20 bp or more, 30 bp or more, 40 bp or more, 50 bp or more, 60 bp or more, 70 bp or more, 80 bp or more, 90 bp or more, 100 bp or more, 110 bp or more, 120 bp or more, 130 bp or more, 140 bp or more, 150 bp or more, 175 bp or more, 200 bp or more, 250 bp or more, 300 bp or more, 350 bp or more, 400 bp or more, 450 bp or more, 500 bp or more, 550 bp or more, or 600 bp or more of flanking sequence that are (i) upstream of (i.e., located 5' to) the relevant marker allele and/or (ii) downstream of (i.e., located 3' to) the relevant marker allele. Thus, in particular examples, the disclosed marker can be detected by amplifying nucleic acid (e.g., genomic DNA) sequence to produce an amplicon comprising one or more of the marker allele sequences identified in Tables 1-8 herein. Primers suitable for amplification of each marker are disclosed Tables 1-8.

Additionally, the markers disclosed herein can be detected by nucleotide sequencing of nucleic acids such as genomic DNA (e.g., by first amplifying genomic sequence and sequencing the resulting amplicon) comprising a resistance marker allele sequence identified in Tables 1-8 for each of the disclosed CrB8, CrG8, CrE8, CrM8, and CrI8 loci, respectively.

Other methods of detecting the marker allele for the CrB8, CrG8, CrE8, CrM8, and CrI8 loci disclosed herein include single base extension (SBE) methods, which involve the extension of a nucleotide primer that is adjacent to a polymorphism to incorporate a detectable nucleotide residue upon extension of the primer through the polymorphism, e.g., extension through the marker allele disclosed herein.

Methods of detecting the marker allele for the CrB8, CrG8, CrE8, CrM8, and CrI8 loci disclosed herein also include LCR; and transcription-based amplification methods (e.g., SNP detection, SSR detection, RFLP analysis, and others). Useful techniques include hybridization of a probe nucleic acid to a nucleic acid corresponding to a marker allele disclosed herein, or a linked marker (e.g., an amplified nucleic acid produced using a genomic canola DNA molecule as a template). Hybridization formats including, for example and without limitation, solution phase; solid phase; mixed phase; and in situ hybridization assays may be useful for allele detection in particular embodiments. An extensive guide to hybridization of nucleic acids is discussed in Tijssen, Laboratory Techniques in Biochemistry and Molecular Biology-Hybridization with Nucleic Acid Probes (Elsevier, NY. 1993).

Many detection methods (including amplification-based and sequencing-based methods) may be readily adapted to high throughput analysis in some examples, for example, by using available high throughput sequencing methods, such as sequencing by hybridization.

Detecting each of the CrB8, CrG8, CrE8, CrM8, and CrI8 loci (or marker allele therefor) disclosed herein can be done using nucleotide sequencing products, amplicons, or probes comprising detectable labels. Detectable labels suitable for use include any composition that can be detected by spectroscopic, radioisotopic, photochemical, biochemical, immunochemical, electrical, optical, or chemical means. Thus, a particular allele of a SNP may be detected using, for example, autoradiography, fluorography, or other similar detection techniques, depending on the particular label to be detected. Useful labels include biotin (for staining with labeled streptavidin conjugate), magnetic beads, fluorescent dyes, radiolabels, enzymes, luminescent or phosphorescent indicators, and colorimetric labels. Other labels include ligands that bind to antibodies or specific binding targets labeled with fluorophores, chemiluminescent agents, and enzymes. In some examples the detection techniques disclosed herein include the use of fluorescent dyes (e.g. FAM, VIC, TET, FITC, TRITC, Texas Red, etc.) with or without a quencher (BHQ1 or DABsyl).

Marker Assisted Selection

Molecular markers can be used in a variety of plant breeding applications (e.g. see Staub et al. (1996) *Hortscience* 31: 729-741; Tanksley (1983) *Plant Molecular Biology Reporter.* 1: 3-8). A molecular marker that demonstrates linkage with a locus affecting a desired phenotypic trait provides a useful tool for the selection of the trait in a plant population. This is particularly true where the phenotype is hard to assay. Since DNA marker assays are less laborious and take up less physical space than field phenotyping, much larger populations can be assayed, increasing the chances of finding a recombinant with the target segment from the donor line moved to the recipient line. Thus, marker-assisted selection (MAS) has been used to significantly increase the efficiency of plant breeding at least in part by improving the efficiency of backcrossing and gene introgression.

The closer the linkage between marker and locus, the more useful the marker, as recombination is less likely to occur between the marker and the genomic feature that causes the trait, which can result in false positives. Having flanking markers on both sides of a locus decreases the chances that false positive selection will occur as a double recombination event would be needed. Generally, it is most preferred to have a marker within or at the genomic locus (e.g., within the gene or at the mutation that causes the phenotype) itself, so that recombination cannot occur between the marker and the causal gene or mutation. In some embodiments, the methods disclosed herein produce a marker in a disease resistance gene, wherein the gene was identified by inferring genomic location from clustering of conserved domains or a clustering analysis.

When a gene is introgressed by MAS, it is not only the gene that is introduced but also the flanking regions (Gepts (2002). *Crop Sci,* 42: 1780-1790). This is referred to as "linkage drag." In the case where the donor plant is highly unrelated to the recipient plant, these flanking regions carry additional genes that may code for agronomically undesirable traits. This "linkage drag" may also result in reduced yield or other negative agronomic characteristics even after multiple cycles of backcrossing into the elite line. This is also sometimes referred to as "yield drag." The size of the flanking region can be decreased by additional backcrossing, although this is not always successful, as breeders do not have control over the size of the region or the recombination breakpoints (Young et al. (1998) *Genetics* 120:579-585). In classical breeding it is usually only by chance that recombinations are selected that contribute to a reduction in the size of the donor segment (Tanksley et al. (1989). *Biotechnology* 7: 257-264). Even after 20 backcrosses in backcrosses of this type, one may expect to find a sizeable piece of the donor chromosome still linked to the gene being selected. With markers however, it is possible to select those rare individuals that have experienced recombination near the gene of interest. In 150 backcross plants, there is a 95% chance that at least one plant will have experienced a crossover within 1 cM of the gene, based on a single meiosis map distance. Markers will allow unequivocal identification of those individuals. With one additional backcross of 300 plants, there would be a 95% chance of a crossover within 1 cM single meiosis map distance of the other side of the gene, generating a segment around the target gene of less than 2 cM based on a single meiosis map distance. This can be accomplished in two generations with markers, while it would have required on average 100 generations without markers (See Tanksley et al., supra). When the exact location of a gene is known, flanking markers surrounding the gene can be utilized to select for recombinations in different population sizes. For example, in smaller population sizes, recombinations may be expected further away from the gene, so more distal flanking markers would be required to detect the recombination.

Important components to the implementation of MAS are: (i) defining the population within which the marker-trait association will be determined, which can be a segregating population, or a random or structured population; (ii) monitoring the segregation or association of polymorphic markers relative to the trait, and determining linkage or association using statistical methods; (iii) defining a set of desirable markers based on the results of the statistical analysis, and (iv) the use and/or extrapolation of this information to the current set of breeding germplasm to enable marker-based selection decisions to be made. The markers described in this disclosure, as well as other marker types such as SSRs and FLPs, can be used in marker assisted selection protocols.

SSRs can be defined as relatively short runs of tandemly repeated DNA with lengths of 6 bp or less (Tautz (1989) *Nucleic Acid Research* 17: 6463-6471; Wang et al. (1994) *Theoretical and Applied Genetics,* 88:1-6) Polymorphisms arise due to variation in the number of repeat units, probably caused by slippage during DNA replication (Levinson and Gutman (1987) Mol Biol Evol 4: 203-221). The variation in repeat length may be detected by designing PCR primers to the conserved non-repetitive flanking regions (Weber and May (1989) *Am J Hum Genet.* 44:388-396). SSRs are highly suited to mapping and MAS as they are multi-allelic, codominant, reproducible and amenable to high throughput automation (Rafalski et al. (1996) Generating and using DNA markers in plants. In: *Non-mammalian genomic analysis: a practical guide*. Academic press. pp 75-135).

Various types of SSR markers can be generated, and SSR profiles can be obtained by gel electrophoresis of the amplification products. Scoring of marker genotype is based on the size of the amplified fragment.

Various types of FLP markers can also be generated. Most commonly, amplification primers are used to generate fragment length polymorphisms. Such FLP markers are in many ways similar to SSR markers, except that the region amplified by the primers is not typically a highly repetitive region. Still, the amplified region, or amplicon, will have sufficient variability among germplasm, often due to insertions or deletions, such that the fragments generated by the amplification primers can be distinguished among polymorphic individuals, and such indels are known to occur frequently in maize (Bhattramakki et al. (2002). *Plant Mol Biol* 48, 539-547; Rafalski (2002b), supra).

SNP markers detect single base pair nucleotide substitutions. Of all the molecular marker types, SNPs are the most abundant, thus having the potential to provide the highest genetic map resolution (Bhattramakki et al. 2002 *Plant Molecular Biology* 48:539-547). SNPs can be assayed at an even higher level of throughput than SSRs, in a so-called ‘ultra-high-throughput’ fashion, as SNPs do not require large amounts of DNA and automation of the assay may be straight-forward. SNPs also have the promise of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing, and coded spheres. Such methods have been reviewed in: Gut (2001) *Hum Mutat* 17 pp. 475-492; Shi (2001) *Clin Chem* 47, pp. 164-172; Kwok (2000) *Pharmacogenomics* 1, pp. 95-100; and Bhattramakki and Rafalski (2001) Discovery and application of single nucleotide polymorphism markers in plants. In: R. J. Henry, Ed, *Plant Genotyping: The DNA Fingerprinting of Plants*, CABI Publishing, Wallingford. A wide range of commercially available technologies utilize these and other methods to interrogate SNPs including Masscode™ (Qiagen), INVADER®. (Third Wave Technologies) and Invader PLUS®, SNAPSHOT®. (Applied Biosystems), TAQMAN®. (Applied Biosystems) and BEADARRAYS®. (Illumina).

A number of SNPs together within a sequence, or across linked sequences, can be used to describe a haplotype for any particular genotype (Ching et al. (2002), *BMC Genet.* 3:19 pp Gupta et al. 2001, Rafalski (2002b), *Plant Science* 162:329-333). Haplotypes can be more informative than single SNPs and can be more descriptive of any particular genotype. For example, a single SNP may be allele “T” for a specific line or variety with disease resistance, but the allele ‘T’ might also occur in the breeding population being utilized for recurrent parents. In this case, a haplotype, e.g. a combination of alleles at linked SNP markers, may be more informative. Once a unique haplotype has been assigned to a donor chromosomal region, that haplotype can be used in that population or any subset thereof to determine whether an individual has a particular gene. See, for example, WO2003054229. Using automated high throughput marker detection platforms makes this process highly efficient and effective.

Many of the markers presented herein can readily be used as single nucleotide polymorphic (SNP) markers to select for clubroot resistance. Using PCR, the primers are used to amplify DNA segments from individuals (preferably inbred) that represent the diversity in the population of interest. The PCR products are sequenced directly in one or both directions. The resulting sequences are aligned and polymorphisms are identified. The polymorphisms are not limited to single nucleotide polymorphisms (SNPs), but also include indels, CAPS, SSRs, and VNTRs (variable number of tandem repeats). Specifically, with respect to the fine map information described herein, one can readily use the information provided herein to obtain additional polymorphic SNPs (and other markers) within the region amplified by the primers disclosed herein. Markers within the described map region can be hybridized to BACs or other genomic libraries, or electronically aligned with genome sequences, to find new sequences in the same approximate location as the described markers.

In addition to SSR’s, FLPs and SNPs, as described above, other types of molecular markers are also widely used, including but not limited to expressed sequence tags (ESTs), SSR markers derived from EST sequences, randomly amplified polymorphic DNA (RAPD), and other nucleic acid based markers.

Isozyme profiles and linked morphological characteristics can, in some cases, also be indirectly used as markers. Even though they do not directly detect DNA differences, they are often influenced by specific genetic differences. However, markers that detect DNA variation are far more numerous and polymorphic than isozyme or morphological markers (Tanksley (1983) *Plant Molecular Biology Reporter* 1:3-8).

Sequence alignments or contigs may also be used to find sequences upstream or downstream of the specific markers listed herein. These new sequences, close to the markers described herein, are then used to discover and develop functionally equivalent markers. For example, different physical and/or genetic maps are aligned to locate equivalent markers not described within this disclosure but that are within similar regions. These maps may be within the species, or even across other species that have been genetically or physically aligned.

In general, MAS uses polymorphic markers that have been identified as having a significant likelihood of co-segregation with a trait such as the clubroot disease resistance traits disclosed herein. Such markers are presumed to map near a gene or genes that give the plant its disease resistant phenotype, and are considered indicators for the desired trait, or markers. Plants are tested for the presence of a desired allele in the marker, and plants containing a desired genotype at one or more loci are expected to transfer the desired genotype, along with a desired phenotype, to their progeny. Thus, plants with clubroot disease resistance may be selected for by detecting one or more marker alleles, and in addition, progeny plants derived from those plants can also be selected. Hence, a plant containing a desired genotype in a given chromosomal region (i.e. a genotype associated with disease resistance) is obtained and then crossed to another plant. The progeny of such a cross would then be evaluated genotypically using one or more markers and the progeny plants with the same genotype in a given chromosomal region would then be selected as having disease resistance.

The markers disclosed herein can be used alone or in combination (i.e. as haplotype) to select for a favorable clubroot resistance locus. For example, each SNP having the resistance allele disclosed in Table 1 (e.g., N101BW0-001-Q001 having the "A" allele at position 10 of SEQ ID NO:1) can be used alone or in combination with another SNP resistance allele (e.g., the N101BW0-001-Q001 having "T" allele and N101BW2-001-Q001 having the "T" allele at position 12 of SEQ ID NO:5), or a combination thereof.

The skilled artisan would expect that there might be additional polymorphic sites at marker loci in and around a chromosome marker identified by the methods disclosed herein, wherein one or more polymorphic sites is in linkage disequilibrium (LD) with an allele at one or more of the polymorphic sites in the haplotype and thus could be used in a marker assisted selection program to introgress a gene allele or genomic fragment of interest. Two particular alleles at different polymorphic sites are said to be in LD if the presence of the allele at one of the sites tends to predict the presence of the allele at the other site on the same chromosome (Stevens, *Mol. Diag.* 4:309-17 (1999)). The marker loci can be located within 5 cM, 2 cM, or 1 cM (on a single meiosis based genetic map) of the disease resistance trait QTL.

The skilled artisan would understand that allelic frequency (and hence, haplotype frequency) can differ from one germplasm pool to another. Germplasm pools vary due to maturity differences, heterotic groupings, geographical distribution, etc. As a result, SNPs and other polymorphisms may not be informative in some germplasm pools.

While the invention has been particularly shown and described with reference to a preferred embodiment and various alternate embodiments, it will be understood by persons skilled in the relevant art that various changes in form and details can be made therein without departing from the spirit and scope of the invention. For instance, while the particular examples below may illustrate the methods and embodiments described herein using a specific plant, the principles in these examples may be applied to any plant. Therefore, it will be appreciated that the scope of this invention is encompassed by the embodiments of the inventions recited herein and in the specification rather than the specific examples that are exemplified below. All cited patents and publications referred to in this application are herein incorporated by reference in their entirety, for all purposes, to the same extent as if each were individually and specifically incorporated by reference.

EXAMPLES

The following are examples of specific aspects of the invention. The examples are offered for illustrative purposes only, and are not intended to limit the scope of the invention in any way.

Example 1: Screening for Disease Resistance. Corteva Agriscience conducted a large, nearly decade-long research program to identify new, major genetic sources of disease resistance in *Brassica*. This effort included large-scale genetic screens of *Brassica napus* (winter oilseed rape and canola), *Brassica napus* vegetable form (rutabaga) and *Brassica rapa* (Chinese cabbage and stubble turnip) species which share common genomes. Extensive inter-specific pre-breeding was carried out to introgress resistance gene sources, eliminate linkage drag, characterize their efficacy in different genetic backgrounds, and locate their genomic positions by linkage mapping. One product of this effort was the identification of the genomic hot spots and proprietary markers for clubroot resistance disclosed in the following Examples.

Example 2: Clubroot resistance locus CrB8. Major clubroot resistance locus CrB8 was identified and its genetic position was located to the interval flanked by and including 12.94 cM and 16.44 cM on chromosome N8. One source of this resistance locus has been identified in SW Rebus spring turnip rape from Sweden (see e.g., Tanhuanpaa et al., 2016, *Genome* 59(1): 11-21). The physical position of CrB8 was mapped using proprietary genomic maps to the locus corresponding to nucleotide position 10,656,081 to position 13,303,318 of chromosome N8 of a non-proprietary *Brassica napus* reference genome. Gene markers were identified within the chromosomal interval and then converted to TaqMan™ (Thermo Fisher, Waltham, MA) assays. CrB8 marker name (NAME), physical position (POS), its resistance allele (RES) and susceptible allele (SUS), SEQ ID NO, and corresponding sequences for assay primers and probes are described in Table 1. These assays were tested on a canola diversity panel comprised of approximately 350 elite lines and hybrids representing the genetic diversity of the proprietary germplasm. Assays were also tested on a canola donor panel comprised of clubroot resistant donor lines. The purpose of both canola panel screenings was to confirm donor specificity of the markers. TaqMan™ markers were also tested on two proprietary DH mapping population to confirm marker-trait association. Finally, the TaqMan™ markers were tested on two F2 mapping populations to validate the markers' technical performance. In Table 1 and in Tables 2-8 herein, the single nucleotide polymorphism SNP for each resistance and susceptibility allele sequence is indicated by bold and underlined text.

TABLE 1

| NAME | POS (bp) | RES | SUS | SEQ ID NO: | SEQUENCE | FUNCTION |
|---|---|---|---|---|---|---|
| N101BW0-001-Q001 | 10910949 | T | G | 1 | TCTCTCTAC**<u>A</u>**GTTTTGG | FAM Probe for RES |
| | | | | 2 | TCTCTAC**<u>C</u>**GTTTTGGTG | VIC Probe for SUS |
| | | | | 3 | CAATTTCATTATCGTATCTGCAAATT | Forward Primer |
| | | | | 4 | TATGCGGCATTGGTTTCTTG | Reverse Primer |

TABLE 1-continued

| NAME | POS (bp) | RES | SUS | SEQ ID NO: | SEQUENCE | FUNCTION |
|---|---|---|---|---|---|---|
| N101BW 2-001- Q001 | 11314585 | A | T | 5 | ATGGTGTTACTCCGCCT | FAM Probe for RES |
| | | | | 6 | ATGGTGTTACACCGCC | VIC Probe for SUS |
| | | | | 7 | AGTGGAAGAGTTCCCTGATGAG | Forward Primer |
| | | | | 8 | TGGACCACTATAAACGAGGCTAA | Reverse Primer |
| N101BW 2-001- Q002 | 11314585 | A | T | 5 | ATGGTGTTACTCCGCCT | FAM Probe for RES |
| | | | | 6 | ATGGTGTTACACCGCC | VIC Probe for SUS |
| | | | | 7 | AGTGGAAGAGTTCCCTGATGAG | Forward Primer |
| | | | | 9 | ACGAGGCTAATATATTCACTATTGGAG | Reverse Primer |
| N101BW 2-001- Q003 | 11314585 | A | T | 5 | ATGGTGTTACTCCGCCT | FAM Probe for RES |
| | | | | 6 | ATGGTGTTACACCGCC | VIC Probe for SUS |
| | | | | 10 | ACCTACGATATATGGTTCAGTGGAA | Forward Primer |
| | | | | 8 | TGGACCACTATAAACGAGGCTAA | Reverse Primer |
| N101BW 2-001- Q004 | 11314585 | A | T | 5 | ATGGTGTTACTCCGCCT | FAM Probe for RES |
| | | | | 6 | ATGGTGTTACACCGCC | VIC Probe for SUS |
| | | | | 10 | ACCTACGATATATGGTTCAGTGGAA | Forward Primer |
| | | | | 9 | ACGAGGCTAATATATTCACTATTGGAG | Reverse Primer |
| N101BW 3-001- Q001 | 11316993 | A | G | 11 | CACCACTTTGTTAAAA | FAM Probe for RES |
| | | | | 12 | CACCACTTTGTCAAAA | VIC Probe for SUS |
| | | | | 13 | GGTGGTTTTGCCCTTGTAAA | Forward Primer |
| | | | | 14 | CCAAATTCTGGTTCTTCTGACAA | Reverse Primer |
| N101BW 5-001- Q001 | 11505014 | C | T | 15 | CTACAGTATAAATTTCCAC | FAM Probe for SUS |
| | | | | 16 | CCTACAGTATAAATCTC | VIC Probe for RES |
| | | | | 17 | CCTTAGAAATTTCACACAAGTTGATT | Forward Primer |
| | | | | 18 | CAAGTTCTTTAAGGAAAGAGAGAGGTT | Reverse Primer |
| N101BW 5-001- Q002 | 11505014 | C | T | 15 | CTACAGTATAAATTTCCAC | FAM Probe for SUS |
| | | | | 16 | CCTACAGTATAAATCTC | VIC Probe for RES |
| | | | | 19 | GAAGGAACCTTAGAAATTTCACACA | Forward Primer |
| | | | | 18 | CAAGTTCTTTAAGGAAAGAGAGAGGTT | Reverse Primer |
| N101BW A-001- Q001 | 11316941 | G | C | 20 | ATTCTCATCGCATCTT | FAM Probe for RES |
| | | | | 21 | TCTCATCGGATCTTT | VIC Probe for SUS |
| | | | | 13 | GGTGGTTTTGCCCTTGTAAA | Forward Primer |
| | | | | 14 | CCAAATTCTGGTTCTTCTGACAA | Reverse Primer |
| N101BW B-001- Q001 | 11319495 | C | A | 22 | CACGTTTTGTTTACATCG | FAM Probe for SUS |
| | | | | 23 | CACGTTTTGTTTCCA | VIC Probe for RES |
| | | | | 24 | AATAGGCTTATCACCTCCTTGTTTAA | Forward Primer |
| | | | | 25 | GGCAGAAGTGGATGGGGTA | Reverse Primer |
| N101BW B-001- Q002 | 11319495 | C | A | 22 | CACGTTTTGTTTACATCG | FAM Probe for SUS |
| | | | | 23 | CACGTTTTGTTTCCA | VIC Probe for RES |
| | | | | 26 | GCAACTAATAGGCTTATCACCTCCTT | Forward Primer |
| | | | | 25 | GGCAGAAGTGGATGGGGTA | Reverse Primer |
| N101BW C-001- Q001 | 11319505 | C | T | 27 | ATCGCTCCTGCAAC | FAM Probe for SUS |
| | | | | 28 | ATCGCTCCCGCAAC | VIC Probe for RES |
| | | | | 24 | AATAGGCTTATCACCTCCTTGTTTAA | Forward Primer |
| | | | | 25 | GGCAGAAGTGGATGGGGTA | Reverse Primer |
| N101BW C-001- Q002 | 11315059 | C | T | 27 | ATCGCTCCTGCAAC | FAM Probe for SUS |
| | | | | 28 | ATCGCTCCCGCAAC | VIC Probe for RES |
| | | | | 26 | GCAACTAATAGGCTTATCACCTCCTT | Forward Primer |
| | | | | 25 | GGCAGAAGTGGATGGGGTA | Reverse Primer |

Each TaqMan™ assay for this Example (as well as the remaining Examples 3-8 herein) was performed using 13.6 µl of a primer probe mixture (18 µM of each probe, 4 µM of each primer) and 1000 µl of master mix from ToughMix™ kit (Quanta Beverly, MA). A liquid handler dispensed 1.3 µl of the mix onto a 1536 well plate containing ~6 ng of dried DNA. The plate was sealed with a laser sealer and thermocycled in a Hydrocycler device (LGC Genomic Limited, Middlesex, United Kingdom) under the following conditions: 94° C. for 15 min, 40 cycles of 94° C. for 30 secs, 60° C. for 1 min. PCR products are measured using at wavelengths 485 (FAM) and 520 (VIC) by a Pherastar™ plate reader (BMG Labtech, Offenburg, Germany). The values are normalized against ROX and plotted and scored on scatterplots utilizing the Kraken™ software.

Marker N101BW0-001-Q001 was found to be particularly tightly linked to resistance locus CrB8 and was uniquely specific to resistant donor lines.

Additional TaqMan™ markers were designed based on whole genome sequencing (WGS) data (Table 2). All markers were located within a 300 kb segment that does not include any of the markers identified in Table 1. Allele specificity was assessed using in silico WGS reads of the clubroot resistant donor and elite inbred susceptible germplasm. The selected markers can be used together as a haplotype. Donor specificity of the markers was determined using in silico WGS read data. Each marker (NAME), physical position (POS), its resistance allele (RES) and susceptible allele (SUS), SEQ ID NO, and corresponding sequences for assay primers and probes are described in Table 2.

TABLE 2

| NAME | POS (bp) | RES | SUS | SEQ ID NO: | SEQUENCE | FUNCTION |
|---|---|---|---|---|---|---|
| N101T3 | 11021258 | A | T | 29 | ATCTGTACATGTGAAACA | FAM Probe for SUS |
| M-001- | | | | 30 | ATCTGTACATGAGAAAC | VIC Probe for RES |
| Q001 | | | | 31 | AACAAGTGTGATTCTCATTTCCAA | Forward Primer |
| | | | | 32 | TGAGATGAAGACACATTCACACA | Reverse Primer |
| N101T3 | 11167528 | A | G | 33 | TTGTTTAAACTCTGGTTCC | FAM Probe for RES |
| P-001- | | | | 34 | TTGTTTAAGCTCTGGTTC | VIC Probe for SUS |
| Q001 | | | | 35 | GTGTCCCACCATTCTCTGCT | Forward Primer |
| | | | | 36 | TCAATTGGTAGTTATAATGTTGTG<br>AGC | Reverse Primer |
| N101T3 | 11167547 | T | C | 37 | TTCCACTTGTCTTGATG | FAM Probe for RES |
| R-001- | | | | 38 | TTCCACTTGTCTCGATG | VIC Probe for SUS |
| Q001 | | | | 35 | GTGTCCCACCATTCTCTGCT | Forward Primer |
| | | | | 36 | TCAATTGGTAGTTATAATGTTGT<br>GAGC | Reverse Primer |

The clubroot resistance markers in Tables 1 and 2 are very tightly linked to the CrB8 locus; each has an LOD score of 30 or greater. Furthermore, each of the markers was tested in two different mapping populations. Each test populations included at least 180 individuals. In both test populations, each of the marker alleles listed in Tables 1 and 2 demonstrated 100% association with the clubroot resistance and clubroot susceptibility traits.

Example 3: Clubroot resistance locus CrG8. Another major clubroot resistance locus CrG8 was identified and located to chromosomal interval flanked by and including 13.94 cM and 14.07 cM of chromosome N8. One source of this resistance locus has been identified in Gelria R European turnip (see, e.g., Hirai, M., 2006, *Breeding Science* 54: 223-229). The physical position of CrG8 was mapped using proprietary genomic maps to the locus corresponding to nucleotide position 11,124,294 to position 11,338,475 of chromosome N8 of a non-proprietary *Brassica napus* reference genome. Genetic markers located within the chromosomal interval were converted to TaqMan™ assays. Each CrG8 marker (NAME), physical position (POS), its resistance allele (RES) and susceptible allele (SUS), SEQ ID NO, and corresponding sequences for assay primers and probes are described in Table 3. These assays were tested on a canola diversity panel comprised of approximately 350 elite lines and hybrids representing the genetic diversity of the proprietary germplasm and a clubroot donor panel comprised of clubroot resistant donor lines. The purpose of the panel screenings was to confirm donor specificity of the markers. The TaqMan™ markers were also tested on a proprietary DH mapping population to confirm the marker-trait association and four proprietary F2 mapping populations to evaluate the markers' technical performance.

TABLE 3

| NAME | POS (bp) | RES | SUS | SEQ ID NO: | SEQUENCE | FUNCTION |
|---|---|---|---|---|---|---|
| N100C5 | 11124294 | T | C | 39 | CTTATATCAATCGTGATTTC | FAM Probe for SUS |
| V-001- | | | | 40 | CTCTTATATCAATCATGATTTC | VIC Probe for RES |
| Q001 | | | | 41 | CTCGATCCATAATGTTTCTA<br>ATCAAAAGGC | Forward Primer |
| | | | | 42 | CCTCAGATTCCCTTATCTTGTCGAT | Reverse Primer |
| N100C6 | 11338475 | A | T | 43 | CCTCACAAAACAAAG | FAM Probe for SUS |
| A-001- | | | | 44 | TCCCTCACAATACAAAG | VIC Probe for RES |
| Q001 | | | | 45 | CCAAAGGATGTGACAGAGAGGTAAA | Forward Primer |
| | | | | 46 | ACAGATGAACAAAACATGATATAACAG<br>ACTCTT | Reverse Primer |
| N100C7 | 11153988 | C | T | 47 | TTTTAGTTAACATTGATTTATTAC | FAM Probe for SUS |
| R-001- | | | | 48 | ATTTTAGTTAACATTGATTTGTTAC | VIC Probe for RES |
| Q001 | | | | 49 | CTGTTGAGAAAAAATCTAACAAAATCTT<br>ACTTAAAAATTT | Forward Primer |
| | | | | 50 | CACATATCACTTCTATTTTTATATAA<br>TACCGAATAGAATTATAGAAT | Reverse Primer |

TABLE 3-continued

| NAME | POS (bp) | RES | SUS | SEQ ID NO: | SEQUENCE | FUNCTION |
|---|---|---|---|---|---|---|
| N100C7Y-001-Q001 | 11123059 | G | A | 51 | TCCGGAGT**A**AAGAGTG | FAM Probe for SUS |
| | | | | 52 | CCGGAGT**G**AAGAGTG | VIC Probe for RES |
| | | | | 53 | GCCTCTTTTAGGTTTGGGTTGGA | Forward Primer |
| | | | | 54 | CCGGCCCAGATGGGTTAAA | Reverse Primer |
| N100C84-001-Q001 | 11338868 | T | C | 55 | CTTAGTTTTGGAACGCA**C**CA | FAM Probe for SUS |
| | | | | 56 | CTTAGTTTTGGAACGCA**T**CA | VIC Probe for RES |
| | | | | 57 | CCCACGGAAAAGTCTATACAACTGA | Forward Primer |
| | | | | 58 | GTCGTCGTGGTTGTGATGATATCT | Reverse Primer |
| N100C87-001-Q001 | 11270978 | A | G | 59 | TGGCGTATAAGAA**G**CAATAA | FAM Probe for SUS |
| | | | | 60 | TGGCGTATAAGAA**A**CAATAA | VIC Probe for RES |
| | | | | 61 | TCAATACTAGGTATATACATACTTGTTTGCTAAGTGA | Forward Primer |
| | | | | 62 | CTAGAGTGTCTACGCATTTTGAAGAGA | Reverse Primer |
| N100C86-001-Q001 | 11339261 | A | G | 63 | ACACTCA**G**CAAAGCA | FAM Probe for SUS |
| | | | | 64 | CACACTCA**A**CAAAGCA | VIC Probe for RES |
| | | | | 65 | GCAAATAACAAATCCAGACAGAACCAA | Forward Primer |
| | | | | 66 | TGCAACCTTGTCCTATCAGTTCAAT | Reverse Primer |
| N100C7M-001-Q001 | 11359435 | G | T | 67 | AAACTTGTTTA**T**TTTTCG | FAM Probe for SUS |
| | | | | 68 | CAAACTTGTTTA**G**TTTTCG | VIC Probe for RES |
| | | | | 69 | ATCTTCACATTCCTGCATTGTTTTTGTT | Forward Primer |
| | | | | 70 | ATTGTTGAAAGTTTTAGCTGTTTCAAATTAACAT | Reverse Primer |
| N100CAM-001-Q001 | 10862403 | G | A | 71 | TTCGATTTATCTC**T**TTTTTT | FAM Probe for SUS |
| | | | | 72 | TTTCGATTTATCTC**C**TTTTTT | VIC Probe for RES |
| | | | | 73 | AGACTGCGGTATCAGGTAAAAACAA | Forward Primer |
| | | | | 74 | CGAACTCGAGAGCCAATCCAAATT | Reverse Primer |
| N100CAN-001-Q001 | 11380539 | G | A | 75 | TTTAGTAGCCA**A**TCATGATT | FAM Probe for SUS |
| | | | | 76 | TTTAGTAGCCA**G**TCATGATT | VIC Probe for RES |
| | | | | 77 | CGTTAACATTTCATTGGTTAAATTAGCGTTT | Forward Primer |
| | | | | 78 | CATATTACGGTTTATCTTGGGTAAGAGGTTAAAT | Reverse Primer |
| N100CAP-001-Q001 | 11384118 | G | A | 79 | CACCAAGAAAC**A**AAAA | FAM Probe for SUS |
| | | | | 80 | CATCACCAAGAAAC**G**AAAA | VIC Probe for RES |
| | | | | 81 | CGGAAGGATGATGATGAAGTGAAATAC | Forward Primer |
| | | | | 82 | GATTCAGTTTCGCTTCATCTTCGTT | Reverse Primer |
| N100CAR-001-Q001 | 11384154 | G | A | 83 | ACTGAATCAAA**A**CAAAAG | FAM Probe for SUS |
| | | | | 84 | ACTGAATCAAA**G**CAAAAG | VIC Probe for RES |
| | | | | 85 | ACAGATTCTACAGGATCATCACCAAGA | Forward Primer |
| | | | | 86 | GCTTCGATTGATCTGGATTCAAGCT | Reverse Primer |
| N100C5P-001-Q001 | 11384646 | T | C | 87 | CACATTTT**C**AAATTATG | FAM Probe for SUS |
| | | | | 88 | AGTCACATTTT**T**AAATTATG | VIC Probe |
| | | | | 89 | AGTAACGCGGATTTGTGAGTCAA | Forward Primer |
| | | | | 90 | GCCGGGCTGTCAGTACA | Reverse Primer |
| N100CAT-001-Q001 | 11384688 | G | T | 91 | TTGAAGCCTGTA**T**TTTAGT | FAM Probe for SUS |
| | | | | 92 | TTGAAGCCTGTA**G**TTTAGT | VIC Probe for RES |
| | | | | 93 | GCGTTTTAACTTTTAAGAGGTAGCTTGT | Forward Primer |
| | | | | 94 | GGCCGGGCTGTCAGTAC | Reverse Primer |
| N100C5R-001-Q001 | 11385653 | A | T | 95 | CAGATTTTTGGTATTGTTTT | FAM Probe for SUS |
| | | | | 96 | TTTCAGATTTTTGGTTTTGTTTT | VIC Probe for RES |
| | | | | 97 | CCCGATAATTAATAAAACCCCAATGCAA | Forward Primer |
| | | | | 98 | CCGTCGAATTCAGTTTGGTTGATTT | Reverse Primer |
| N100C5T-001-Q001 | 11386285 | T | C | 99 | CTGATGTTCGTT**C**TATGTC | FAM Probe for SUS |
| | | | | 100 | ACTGATGTTCGTT**T**TATGTC | VIC Probe for RES |
| | | | | 101 | GAATACAAAAATTCTTCAACTTGAAACTTTGGAC | Forward Primer |
| | | | | 102 | ACTAGCAGCAAAATATCAAAATTTCAAAGCA | Reverse Primer |

TABLE 3-continued

| NAME | POS (bp) | RES | SUS | SEQ ID NO: | SEQUENCE | FUNCTION |
|---|---|---|---|---|---|---|
| N100C81-001-Q001 | 11341835 | C | T | 103 | TCAAATAGGAGACGCATCT | FAM Probe for SUS |
| | | | | 104 | CAAATAGGAGGCGCATCT | VIC Probe for RES |
| | | | | 105 | GAGGCATTCTCCTCTTTCACCA | Forward Primer |
| | | | | 106 | CTGGAATCAATTACATCACAACTTTATCAG | Reverse Primer |
| N100CAU-001-Q001 | 11391926 | T | C | 107 | TTTTAATTATTCAGATTATTTTT | FAM Probe for SUS |
| | | | | 108 | ATTTTTAATTATTCAAATTATTTTT | VIC Probe for RES |
| | | | | 109 | TCTTTATTAAACGGAAGAAGTATGTAATT | Forward Primer |
| | | | | 110 | CTGCAATTTGGTTCAGAAAATAAAACTTCTAGTAA | Reverse Primer |
| N100CAV-001-Q001 | 11392121 | T | G | 111 | CGAAAACCCGAAACC | FAM Probe for SUS |
| | | | | 112 | CCGAAAAACCGAAACC | VIC Probe for RES |
| | | | | 113 | GGCTGGGCTTGTACACATGTTAATA | Forward Primer |
| | | | | 114 | CTTAACACATTGGGCCTCAAAGG | Reverse Primer |
| N100CAW-001-Q001 | 11392588 | G | C | 115 | ACCTTGTTGTACTTAGCA | FAM Probe for SUS |
| | | | | 116 | ATACCTTGTTGTAGTTAGCA | VIC Probe for RES |
| | | | | 117 | TGATAAAAAGATTTAGGATATATTACAAAACTTGACCATCA | Forward Primer |
| | | | | 118 | CATTGTAGATGCCTAGGGTTTAAAAGTCTAT | Reverse Primer |
| N100C6E-001-Q001 | 11392602 | T | A | 119 | CATATGACCAAATTTTTTT | FAM Probe for SUS |
| | | | | 120 | CATATGACCAAAATTTTTT | VIC Probe for RES |
| | | | | 121 | CAAAACTTGACCATCAATACCTTGTTGT | Forward Primer |
| | | | | 122 | GCCATTGTAGATGCCTAGGGTTTAA | Reverse Primer |
| N100CAX-001-Q001 | 10654358 | G | A | 123 | ATTTTAAAAAATTTATTATTAATTTT | FAM Probe for SUS |
| | | | | 124 | TTTTAAAAAATTTATTGTTAATTTT | VIC Probe for RES |
| | | | | 125 | TTGTTTAATAAATCAGTTTTTATGGGTTAA | Forward Primer |
| | | | | 126 | TCAACTTAAAGATTTTCAGATTTGTAGATAATTTTTGTTA | Reverse Primer |
| N100C60-001-Q001 | 10655493 | A | G | 127 | TTTTCAACAACTATTCTTG | FAM Prob for SUS |
| | | | | 128 | ATTTTTTCAACAATTATTCTTG | VIC Probe for RES |
| | | | | 129 | GGAGGCCACCTGGACATT | Forward Primer |
| | | | | 130 | AAGAAATATTTTTATTATCAGATGACTATTCCGTGTTTATATACA | Reverse Primer |
| N100CAY-001-Q001 | 10471329 | A | G | 131 | ATACTGGGAAAATTT | FAM Probe for SUS |
| | | | | 132 | CATATATACTGGAAAAAATTT | VIC Probe for RES |
| | | | | 133 | ACTTACAAAATATGTATCCTGACTTTTCATGGT | Forward Primer |
| | | | | 134 | AGTATGAGATTGATTGGGTTTATAAATATTATATA | Reverse Primer |
| N100C6G-001-Q001 | 10473378 | C | G | 135 | CCCAAAGGATCTAAGAAA | FAM Probe for SUS |
| | | | | 136 | CCCAAAGGATGTAAGAAA | VIC Probe for RES |
| | | | | 137 | TTTATGCAATCATTGGCAACACACA | Forward Primer |
| | | | | 138 | CCAGCCGAGAAAGACAACTTGA | Reverse Primer |
| N100C6J-001-Q001 | 10538447 | T | C | 139 | CGTCCAAATATATTGGTGGAG | FAM Probe for SUS |
| | | | | 140 | AGACGTCCAAATATATTAGTGGAG | VIC Probe for RES |
| | | | | 141 | TGGAGGACCAGATTCTGTTTGG | Forward Primer |
| | | | | 142 | TGGCGAAAAAGTCTTTATCCTTTAATTTGAC | Reverse Primer |

Marker N100C6A-001-Q001 was found to be particularly tightly linked to resistance locus CrG8 and was uniquely specific to resistant donor lines.

The clubroot resistance markers in Table 3 are very tightly linked to the CrG8 locus; each has an LOD score of 30 or greater. Furthermore, each of the markers was tested in two different mapping populations. Each test populations included at least 180 individuals. In both test populations, each of the marker alleles listed in Tables 1 and 2 demonstrated 100% association with the clubroot resistance and clubroot susceptibility traits.

Example 4: Clubroot resistance locus CrE8. An additional major clubroot resistance locus, CrE8 was identified and its genetic position was located to interval flanked by and including 12.87 cM and 13.98 cM on chromosome N8. The physical position of CrE8 was mapped using proprietary maps to the locus corresponding to nucleotide position 10,966,500 to 11,124,403 of chromosome N8 of a non-proprietary *Brassica napus* reference genome. Genetic markers linked to CrE8 were converted to TaqMan™ assays. Each CrE8 marker (NAME), physical position (POS), its resistance allele (RES) and susceptible allele (SUS), SEQ ID NO, and corresponding sequences for assay primers and probes are described in Table 4. The assays and tested on a canola diversity panel comprised of approximately 350 elite lines and hybrids representing the genetic diversity of the proprietary germplasm. The purpose of panel screening was to confirm donor specificity of the markers. TaqMan™ markers were also tested on two proprietary DH mapping populations to confirm marker-trait association and an F2 mapping population to validate the markers' technical performance. None of the markers overlap with publicly available 56 k array markers available from Illumina (Madison, WI USA).

TABLE 4

| NAME | POS (bp) | RES | SUS | SEQ ID NO: | SEQUENCE | FUNCTION |
|---|---|---|---|---|---|---|
| N100CJ0-001-Q001 | 10966467 | A | T | 143 | ATTTGTTCTCCC**T**CACAATA | FAM Probe for SUS |
| | | | | 144 | ATTTGTTCTCCC**A**CACAATA | VIC Probe for RES |
| | | | | 145 | CAAGCAGTGGACTATGGTTGGTTA | Forward Primer |
| | | | | 146 | GAGAACCTTCCTCTGTTTCAAACCT | Reverse Primer |
| N100CJI-001-Q001 | 10970941 | T | C | 147 | TCCATC**G**CATTTTT | FAM Probe for SUS |
| | | | | 148 | CTTTCCATC**A**CATTTTT | VIC Probe for RES |
| | | | | 149 | GCATGCTGACGTAAACAACTACATT | Forward Primer |
| | | | | 150 | CGAATAACTGAGTCACGCTTCCT | Reverse Primer |
| N100CJ2-001-Q001 | 10974310 | A | T | 151 | AAGTTACTCAGAC**A**CTCTAC | FAM Probe for SUS |
| | | | | 152 | CAAAGTTACTCAGAC**T**CTCTAC | VIC Probe for RES |
| | | | | 153 | TGGTATGTGTGGAGAGTCTGAAGTT | Forward Primer |
| | | | | 154 | ACACGATTGTGGACGGATGAATTAT | Reverse Primer |
| N100CJ3-001-Q001 | 10975706 | G | A | 155 | CTGATTCACCTC**T**CTCGAC | FAM Probe for SUS |
| | | | | 156 | CTGATTCACCTC**C**CTCGAC | VIC Probe for RES |
| | | | | 157 | GTGTCCACATGCTCAAGAGGTT | Forward Primer |
| | | | | 158 | GTATGCTGCAAATCGATCAGATGTG | Reverse Primer |
| N100CJ4-001-Q001 | 11029403 | T | C | 159 | TCCACTGGCTT**C**TCGTTA | FAM Probe for SUS |
| | | | | 160 | ATCCACTGGCTT**T**TCGTTA | VIC Probe for RES |
| | | | | 161 | TCATGATTTTAAACTTAACCCTGCTCCTT | Forward Primer |
| | | | | 162 | GCATATGACTCTGTTTATCTTCCCTTGT | Reverse Primer |
| N100CJ5-001-Q001 | 11060466 | A | T | 163 | CTAAGGGATGATAA**A**GGA | FAM Probe for SUS |
| | | | | 164 | TTCTAAGGGATGATAA**T**GGA | VIC Probe for RES |
| | | | | 165 | GCATCCCGCTCCCAAGAAA | Forward Primer |
| | | | | 166 | CACCAAGAGATTGGATCAAATGTAATTATTATTATAGTTC | Reverse Primer |
| N100CJ6-001-Q001 | 11101333 | C | T | 167 | CAGCGTTTCATATAT**T**TTTGGAT | FAM Probe for SUS |
| | | | | 168 | CAGCGTTTCATATAT**C**TTTGGAT | VIC Probe for RES |
| | | | | 169 | TTTTTGAGCTAATGGGCCTTCTCT | Forward Primer |
| | | | | 170 | GGTAGGTTTCGTAGGGTAAAAGCT | Reverse Primer |
| N100CJ7-001-Q001 | 11124993 | T | A | 171 | ACATCTCTC**T**CATAAAC | FAM Probe for SUS |
| | | | | 172 | ACATCTCTC**A**CATAAAC | VIC Probe |
| | | | | 173 | TGATTATTAGGGTTTTAATGTGGTGGATTGT | Forward Primer |
| | | | | 174 | GCATCAAGGTGCCTTCTTTAACATG | Reverse Primer |
| N100CJP-002-Q001 | 10927691 | A | G | 175 | CCCTCTGTT**C**GACTACA | FAM Probe for SUS |
| | | | | 176 | ATCCCTCTGTT**T**GACTACA | VIC Probe for RES |
| | | | | 177 | ATCAGAGACTGAGTCTGCATATCCA | Forward Primer |
| | | | | 178 | TCCTCGCATCTTCAAAACTAGTGTT | Reverse Primer |
| N100CJT-001-Q001 | 10966500 | T | C | 179 | CTGTTTCAAACCT**G**AATGT | FAM Probe for SUS |
| | | | | 180 | CTGTTTCAAACCT**A**AATGT | VIC Probe for RES |
| | | | | 181 | AAGCAGTGGACTATGGTTGGTTAAT | Forward Primer |
| | | | | 182 | TCTCACTCAAATGGATTGTGTTCATGT | Reverse Primer |

TABLE 4-continued

| NAME | POS (bp) | RES | SUS | SEQ ID NO: | SEQUENCE | FUNCTION |
|---|---|---|---|---|---|---|
| N100CJV-002-Q001 | 10973102 | G | T | 183 | AGCCGTAAACTAATTAGAG | FAM Probe for SUS |
| | | | | 184 | CAGCCGTAAACTACTTAGAG | VIC Probe for RES |
| | | | | 185 | CTATTCACTTTCAATAATGGCTACGTTGC | Forward Primer |
| | | | | 186 | CAGGCGAGAAGTATGTAAAGTCGTT | Reverse Primer |
| N100CJX-002-Q001 | 10975316 | T | A | 187 | TGGCGGATCTCAAATT | FAM Probe for SUS |
| | | | | 188 | CGTGGCGGATCTCATATT | VIC Probe for RES |
| | | | | 189 | TGTTTGTTTCTTTTGTGGGTTTTGTGA | Forward Primer |
| | | | | 190 | TGAACCTTGATATCATCGTTGTAGACACTATAATA | Reverse Primer |
| N100CK0-002-Q001 | 10975456 | G | T | 191 | ATTTTGTTGTATGAGCTTT | FAM Probe for SUS |
| | | | | 192 | ATTTTGTTGTAGGAGCTTT | VIC Probe for RES |
| | | | | 193 | GGTGGCTTTGAAATTTATCTTAGTAGGTCTT | Forward Primer |
| | | | | 194 | ATTGTGAATCCCATAACGCTTAAGGT | Reverse Primer |
| N100CK2-001-Q001 | 10975634 | C | T | 195 | AACTCTGCAAAGCTT | FAM Probe for SUS |
| | | | | 196 | AACTCTGCGAAGCTT | VIC Probe for RES |
| | | | | 197 | GCTCGATGCCATCTCGTCTAG | Forward Primer |
| | | | | 198 | CTCTTGAGCATGTGGACACTGA | Reverse Primer |
| N100CK4-001-Q001 | 10975658 | G | A | 199 | CGGCCTGGCCCC | FAM Probe for SUS |
| | | | | 200 | CGGCCCGGCCCC | VIC Probe for RES |
| | | | | 201 | GATGCCATCTCGTCTAGTAAGCTT | Forward Primer |
| | | | | 198 | CTCTTGAGCATGTGGACACTGA | Reverse Primer |
| N100CK6-001-Q001 | 10976300 | G | A | 202 | ACTTATTTTAAATCAAAAGTG | FAM Probe for SUS |
| | | | | 203 | TGTACTTATTTTAAATCGAAAGTG | VIC Probe for RES |
| | | | | 204 | AGTTTTGGCAAATTAATTGGAGAGTAGGT | Forward Primer |
| | | | | 205 | CGACCTTATCAATGAGAGACAAAATAATATTAGCA | Reverse Primer |
| N100CK8-002-Q001 | 10977693 | C | T | 206 | CCAACCAAGAAAAT | FAM Probe for SUS |
| | | | | 207 | ATCCAACCAGGAAAAT | VIC Probe for RES |
| | | | | 208 | GTGTCCATCGTCATGAAGATCTCT | Forward Primer |
| | | | | 209 | CAAGTGCCCTTTGTTGAGATTCC | Reverse Primer |
| N100CKA-001-Q001 | 11029667 | C | G | 210 | ACGCAAAAACACTCTGATAA | FAM Probe for SUS |
| | | | | 211 | ACGCAAAAACACTCTCATAA | VIC Probe for RES |
| | | | | 212 | GTTTGAAACTGAAAAAGAGTAGTAAGCACAT | Forward Primer |
| | | | | 213 | GCAAATCACATGTAGCGTTTAAGGT | Reverse Primer |
| N100CKC-002-Q001 | 11124709 | C | A | 214 | CGCGACTCACGCG | FAM Probe for SUS |
| | | | | 215 | CGCGACGCACGCG | VIC Probe for RES |
| | | | | 216 | ACAGAGGCGGGAAGTGTTTATTT | Forward Primer |
| | | | | 217 | TCTTCTTCTTCGTTCGTTTCGGAAA | Reverse Primer |

Marker N100CJT-001-Q001 was found to be particularly tightly linked to resistance locus CrE8 and was uniquely specific for resistant donors.

Additional TaqMan™ markers were designed based on WGS data (Table 5). All markers are located within a 300 kb segment that does not include any of the markers identified in Table 4. Allele specificity was assessed using in silico WGS reads of the donor and elite inbred germplasm. The selected markers can be used together as a haplotype. Each marker's name (NAME), physical position (POS), its resistance allele (RES) and susceptible allele (SUS), SEQ ID NO, and corresponding sequences for assay primers and probes are described in Table 5.

TABLE 5

| NAME | POS (bp) | RES | SUS | SEQ ID NO: | SEQUENCE | FUNCTION |
|---|---|---|---|---|---|---|
| N101T3T-001-Q001 | 11290742 | C | T | 218 | CAGAACTGATGAGTTC | FAM Probe for SUS |
| | | | | 219 | CAGAACTGATGAGTCC | VIC Probe for RES |
| | | | | 220 | GGAAAATGCAAGGAAGAGCA | Forward Primer |
| | | | | 221 | TGAATGATCTCTTTGCTGTGAAA | Reverse Primer |

TABLE 5-continued

| NAME | POS (bp) | RES | SUS | SEQ ID NO: | SEQUENCE | FUNCTION |
|---|---|---|---|---|---|---|
| N101T3U-001-Q001 | 11290750 | A | G | 222 | TTGCTGTGA AATTTTTAA G | FAM Probe for RES |
| | | | | 223 | TTGCTGTGA AATTTTCAA G | VIC Probe for SUS |
| | | | | 224 | CACAAGCAA TTTCAAAGA AGCA | Forward Primer |
| | | | | 225 | TCTCCAATG AAAGAAAAG ATTGG | Reverse Primer |

The clubroot resistance markers in Tables 4 and 5 are very tightly linked to the CrE8 locus; each has an LOD score of 30 or greater. Furthermore, each of the markers was tested in two different mapping populations. Each test populations included at least 180 individuals. In both test populations, each of the marker alleles listed in Tables 4 and 5 demonstrated 100% association with the clubroot resistance and clubroot susceptibility phenotype.

Example 5: Clubroot resistance locus CrM8. One more major clubroot resistance locus CrM8 was identified and its genetic position located to the interval flanked by and including 13.2 cM and 13.38 cM on chromosome N8. One source of this resistance locus has been identified in the *Brassica napus* variety Mendel (see e.g., Fredua-Agyeman et al., 2016, *Euphytica* 211: 201-213). The physical position of CrM8 was mapped using proprietary maps to the locus corresponding to nucleotide position 10,959,267 to position 11,159,261 of chromosome N8 of a non-proprietary *Brassica napus* reference genome. Genetic markers located within this chromosomal interval were converted to TaqMan™ assays. Each marker name (NAME), physical position (POS), its resistance allele (RES) and susceptible allele (SUS), SEQ ID NO, and corresponding sequences for assay primers and probes are described in Table 6. The assays were tested on a *Brassica napus* diversity panel comprised of approximately 350 elite lines and hybrids representing the genetic diversity of the proprietary germplasm and a clubroot donor panel comprising clubroot resistant donor lines. The purpose of the panel screenings was to confirm donor specificity of the markers. TaqMan™ markers were also tested on two proprietary DH mapping population to confirm the marker-trait association and four F2 mapping populations to validate the markers' technical performance. None of the markers overlap with markers on publicly available 56 k array from Illumina.

TABLE 6

| NAME | POS (bp) | RES | SUS | SEQ ID NO | SEQUENCE | FUNCTION |
|---|---|---|---|---|---|---|
| N100CCT-001-Q001 | 10959267 | A | T | 226 | CAAGAGAAAAGAAAGTACTAC | FAM Probe for SUS |
| | | | | 227 | AAGAGAAAAGAAAGAACTAC | VIC Probe for RES |
| | | | | 228 | GGACGAACAGGACTCAAAACTCTAT A | Forward Primer |
| | | | | 229 | GCGCTAACCCCTTTCAAATTCTTAT | Reverse Primer |
| N100CCV-001-Q001 | 11101444 | G | C | 230 | TGTATTTTCCTTTGACAGTAA | FAM Probe for RES |
| | | | | 231 | CTGTATTTTCCTTTCACAGTAA | VIC Probe for SUS |
| | | | | 232 | TTGATGCTACGTATCGAATAAGAAAT GAATAGAA | Forward Primer |
| | | | | 233 | ATCTTGGAAACCCTCTTTGGTGTT | Reverse Primer |
| N100CD4-001-Q001 | 11141347 | C | T | 234 | ACCACCAACAAATAA | FAM Probe for SUS |
| | | | | 235 | CCACCAGCAAATAA | VIC Probe for RES |
| | | | | 236 | TGAGGACTGACAGAATGCACAAG | Forward Primer |
| | | | | 237 | GAGGTAGTGTACATTTGCGACGAT | Reverse Primer |
| N100CD7-001-Q001 | 11145103 | T | A | 238 | ATCTAAGAAACTTTAATTAAAA | FAM Probe for RES |
| | | | | 239 | AGATCTAAGAAACTTTTATTAAAA | VIC Probe for SUS |
| | | | | 240 | GCTTGTCAATGCCTTCCTTGTTA | Forward Primer |
| | | | | 241 | CACATTGAGGTCCATTGATAATATTA GGATGTTA | Reverse Primer |
| N100CD8-001-Q001 | 11145490 | G | C | 242 | CTAGAGAGTATCAAACATC | FAM Probe for RES |
| | | | | 243 | CTAGAGAGTATGAAACATC | VIC Probe for SUS |
| | | | | 244 | ATTTTGTTTGTTTCGTTTGAGTCTTAT CGT | Forward Primer |
| | | | | 245 | TTGACGACTTAATGCATTCACTGAGA | Reverse Primer |
| N100CD9-001-Q001 | 11147445 | A | G | 246 | CACCACGTGTTAGTG | FAM Probe for SUS |
| | | | | 247 | CCACCACATGTTAGTG | VIC Probe for RES |
| | | | | 248 | TTAACTTTTTTTTTCTTTTATTAACCA ATCGCG | Forward Primer |
| | | | | 249 | GGCAAGTTTGGTGAGTTCTTATGGT | Reverse Primer |
| N100CDA-001-Q001 | 11147528 | T | G | 250 | TTTAATAAATTTGTGGGACCC | FAM Probe for RES |
| | | | | 251 | AATAAAGTTGTGGGACCC | VIC Probe for SUS |
| | | | | 252 | CCAAACTTGCCTCTTGCAGAAG | Forward Primer |
| | | | | 253 | TTAGAGCATCATTAACCCCACCTTTT | Reverse Primer |
| N100CDB-001-Q001 | 11147856 | T | C | 254 | CTCACAAGGTGCATACA | FAM Probe for RES |
| | | | | 255 | ACTCACAAGGTGCACACA | VIC Probe for SUS |
| | | | | 256 | CTCACAAGGTGCACTGTTTCAC | Forward Primer |
| | | | | 257 | GGCTTCCAGTCCACAATTATTCCA | Reverse Primer |

TABLE 6-continued

| NAME | POS (bp) | RES | SUS | SEQ ID NO | SEQUENCE | FUNCTION |
|---|---|---|---|---|---|---|
| N100CDC-001-Q001 | 11150527 | C | T | 258 | CATAGTAGTCCAC**A**TGAGTAT | FAM Probe for SUS |
| | | | | 259 | CATAGTAGTCCAC**G**TGAGTAT | VIC Probe for RES |
| | | | | 260 | ACCTTAATCAGTAGACTATAGCGCTTCT | Forward Primer |
| | | | | 261 | GGTTGCTCAATATCGAGACTTTCTTCT | Reverse Primer |
| N100CDD-001-Q001 | 11150839 | G | C | 262 | TTTTCAAAGTAC**C**CCTAATC | FAM Probe for RES |
| | | | | 263 | TTTCAAAGTAC**G**CCTAATC | VIC Probe for SUS |
| | | | | 264 | GTTGTGCACTAATGCATCTCACATT | Forward Primer |
| | | | | 265 | ATGTTCATGTATTGCTCTGCTTTAGTCT | Reverse Primer |
| N100CDF-001-Q001 | 11159141 | G | A | 266 | CAGTGGATG**C**TATGCG | FAM Probe for RES |
| | | | | 267 | TCAGTGGATG**T**TATGCG | VIC Probe for SUS |
| | | | | 268 | TTGTATCCACCAAATGGCATCCA | Forward Primer |
| | | | | 269 | AATAGAGAAGTTGGGCAAGTAAAAGAGATT | Reverse Primer |
| N100CDG-001-Q001 | 11159261 | A | G | 270 | CTTGACCAAAC**C**TTATG | FAM Probe for SUS |
| | | | | 271 | CTTGACCAAAC**T**TTATG | VIC Probe for RES |
| | | | | 272 | TTTTCATGTCAATATTCCCCCTCAAGT | Forward Primer |
| | | | | 273 | GAGGGATGTCTTCATGGTTTCCAA | Reverse Primer |

Marker N100CDD-001-Q001 was found to be particularly tightly linked to resistance locus CrM8 and was uniquely specific for resistant donor lines.

Additional TaqMan™ markers were designed based on WGS data (Table 7). All markers were located within a 300 kb segment that does not include any of the markers identified in Table 6. Allele specificity was assessed using in silico WGS reads of the donor and elite inbred germplasm. The selected markers can be used together as a haplotype. Each additional CrM8 marker's name (NAME), physical position (POS), its resistance allele (RES) and susceptible allele (SUS), SEQ ID NO, and corresponding sequences for assay primers and probes are described in Table 7.

TABLE 7

| NAME | POS (bp) | RES | SUS | SEQ ID NO | SEQUENCE | FUNCTION |
|---|---|---|---|---|---|---|
| N101T3X-001-Q001 | 11341556 | G | A | 274 | TTCGTCCTAGC**A**ACCA | FAM Probe for SUS |
| | | | | 275 | TTCGTCCTAGC**G**ACCA | VIC Probe for RES |
| | | | | 276 | TTTTCATTCAAAAGATCAAAATCA | Forward Primer |
| | | | | 277 | CAACGTGAAATGCAGGTGA | Reverse Primer |
| N101T3Y-001-Q001 | 11341804 | T | G | 278 | CCTCTTTCACCA**T**TATA | FAM Probe for RES |
| | | | | 279 | CTCTTTCACCA**G**TATAT | VIC Probe for SUS |
| | | | | 280 | CCGGATGGAACAGTTCTTTG | Forward Primer |
| | | | | 281 | GGAATCAATTACATCACAACTTTATCAG | Reverse Primer |
| N101T41-001-Q001 | 11478087 | A | G | 282 | TAGCTCCA**A**TTGGTTTT | FAM Probe for RES |
| | | | | 283 | TAGCTCCA**G**TTGGTTTT | VIC Probe for SUS |
| | | | | 284 | GAGGAGCACGGAACAAGATT | Forward Primer |
| | | | | 285 | ACTTGGTCGGCCCAAACTA | Reverse Primer |

The clubroot resistance markers in Tables 6 and 7 are very tightly linked to the CrM8 locus; each has an LOD score of 30 or greater. Furthermore, each of the markers was tested in two different mapping populations. Each test populations included at least 180 individuals. In both test populations, each of the marker alleles listed in Tables 6 and 7 demonstrated 100% association with the clubroot resistance and clubroot susceptibility phenotype.

Example 6: Clubroot resistance locus CrI8. Yet another major clubroot resistance locus, CrI8, was identified and its genetic position was located to the interval flanked by and including 13.2 cM and 13.7 cM on chromosome N8. CrI8 was mapped using proprietary maps to the locus corresponding to nucleotide position 10,986,309 to position 11,500,321 of chromosome N8 of a non-proprietary *Brassica napus* reference genome. Genetic markers located within the chromosomal interval were converted to TaqMan™ assays. Each marker's name (NAME), physical position (POS), its resistance allele (RES) and susceptible allele (SUS), SEQ ID NO, and corresponding sequences for assay primers and probes are described in Table 8. The assays were tested on a *Brassica napus* (canola/oilseed) diversity panel comprised of approximately 350 elite lines and hybrids representing the genetic diversity of the proprietary germplasm and a clubroot donor panel comprised of clubroot resistant donor lines. The purpose of the panel screenings was to confirm donor specificity of the markers. TaqMan™ markers were also tested on a proprietary DH mapping population to confirm the marker-trait association and a proprietary F2 mapping population to validate the technical performance of the TaqMan™ assays.

TABLE 8

| NAME | POS (bp) | RES | SUS | SEQ ID NO: | SEQUENCE | FUNCTION |
|---|---|---|---|---|---|---|
| N101T0M-001-Q001 | 10995424 | G | A | 286 | AATTTTTGAATATCAATTTT | FAM Probe for RES |
| | | | | 287 | TGAAATTTTTGAATATTAATTTT | VIC Probe for SUS |
| | | | | 288 | CCTAGGGTATCAATTTTTAGTTTTTTTTACTAAATGGT | Forward Primer |
| | | | | 289 | CTCGCAAATAATTTTCTTAAGTTTTTGTTACCAAA | Reverse Primer |
| N101T0N-001-Q001 | 10996913 | C | G | 290 | ACCATTCGCGTTTTG | FAM Probe for RES |
| | | | | 291 | ACCATTCGGGTTTTG | VIC Probe for SUS |
| | | | | 292 | TTTTTCGGGTTTGGAAATATAGGA | Forward Primer |
| | | | | 293 | ACCCGAAAACCAAACCAAAACC | Reverse Primer |
| N101T0P-001-Q001 | 10996942 | C | T | 294 | CCGATTTCGGTCTTAGTT | FAM Probe for RES |
| | | | | 295 | TCCGATTTCGGTTTTAGTT | VIC Probe for SUS |
| | | | | 296 | GGGTTTGGAAATATAGGAACCATTCG | Forward Primer |
| | | | | 297 | ACCCGAAAACCAAACCAAAACC | Reverse Primer |
| N101T0R-001-Q001 | 10996958 | T | C | 298 | AACCAAAACCAAACCGA | FAM Probe for RES |
| | | | | 299 | AAACCAAAACCGAACCGA | VIC Probe for SUS |
| | | | | 296 | GGGTTTGGAAATATAGGAACCATTCG | Forward Primer |
| | | | | 300 | TTTAATCTAGAATCTCGTTTAGTTCTGGGC | Reverse Primer |
| N101T0T-001-Q003 | 11155547 | G | A | 301 | CTTGACAAAATATAAGGTT | FAM Probe for SUS |
| | | | | 302 | CTTGACAAAGTATAAGGTT | VIC Probe for RES |
| | | | | 303 | CATGCAATCTTCCAAACTTAAAAAT | Forward Primer |
| | | | | 304 | GTTATTCTTTATTATCTATGGTTTTATCTTTTG | Reverse Primer |
| N101T0U-001-Q001 | 11191065 | G | A | 305 | CACAAACCGAACCAA | FAM Probe for RES |
| | | | | 306 | TTACACAAACCAAACCAA | VIC Probe for SUS |
| | | | | 307 | AATTGGACTCAAAATTATCTTAAATATTAGTTGGT | Forward Primer |
| | | | | 308 | GGGTATAGGTTCGGTTTTATTTGTTCTAGA | Reverse Primer |
| N101T0V-001-Q001 | 11191077 | G | A | 309 | CAAATACCGAAATAAC | FAM Probe for RES |
| | | | | 310 | CCAAATACCAAAATAAC | VIC Probe for SUS |
| | | | | 307 | AATTGGACTCAAAATTATCTTAAATATTAGTTGGT | Forward Primer |
| | | | | 308 | GGGTATAGGTTCGGTTTTATTTGTTCTAGA | Reverse Primer |
| NP1 | 11368007 | C | A | 311 | GGTAACATGTATTCATC | FAM Probe for SUS |
| | | | | 312 | GGTAACATGTCTTCATC | VIC Probe for RES |
| | | | | 313 | TTTGTAGTTGAACAAAGTTGAAGGA | Forward Primer |
| | | | | 314 | AGGGTACGTTGGAAGGGTCT | Reverse Primer |
| NP2 | 11384573 | A | G | 315 | GTAACGCAGATTTGT | FAM Probe for RES |
| | | | | 316 | GTAACGCGGATTTG | VIC Probe for SUS |
| | | | | 317 | CGGCACTAGAATACGATTCCTC | Forward Primer |
| | | | | 318 | AAATGTGACTTAAACAAGCTACCTCTT | Reverse Primer |
| NP3 | 11391245 | T | G | 319 | GTTTGACGTAAAGAAA | FAM Probe for RES |
| | | | | 320 | GTTTGACGGAAAGAA | VIC Probe for SUS |
| | | | | 321 | GGAGGAAGAGATCGGTGATG | Forward Primer |
| | | | | 322 | TGGTAGATGAAACATCCAAGCA | Reverse Primer |

TABLE 8-continued

| NAME | POS (bp) | RES | SUS | SEQ ID NO: | SEQUENCE | FUNCTION |
|---|---|---|---|---|---|---|
| NP4 | 11399507 | A | G | 323 | GATCACTC**A**GTTAAAT | FAM Probe for RES |
| | | | | 324 | GATCACTC**G**GTTAAA | VIC Probe for SUS |
| | | | | 325 | TGGCAATTCCCCATAAATAAA | Forward Primer |
| | | | | 326 | TGTTCATGGTTTTGAAAGTGAAA | Reverse Primer |
| NP5 | 11406704 | A | T | 327 | TACTAG**A**ATGCAACCTT | FAM Probe for RES |
| | | | | 328 | TACTAG**T**ATGCAACCTT | VIC Probe for SUS |
| | | | | 329 | TCAGATTCCAGGATCGAGGT | Forward Primer |
| | | | | 330 | GCTCCACTCGAAATCGTCAC | Reverse Primer |

Marker N101T0T-001-Q003 was found to be particularly tightly linked to resistance locus CrI8 and was uniquely specific for resistant donor lines.

The clubroot resistance markers in Table 8 are very tightly linked to the CrI8 locus; each has an LOD score of 30 or greater. Furthermore, each of the markers was tested in two different mapping populations. Each test populations included at least 180 individuals. In both test populations, each of the marker alleles listed in Table 8 demonstrated 100% association with the clubroot resistance and clubroot susceptibility phenotype.

We claim:

1. A method for introducing a clubroot resistance locus into a *Brassica* plant the method comprising:

crossing a first parent *Brassica* plant comprising CrB8 clubroot resistance locus with a second *Brassica* plant of a different genotype to produce progeny plants;

obtaining a nucleic acid-containing sample from one or more of the progeny plants;

screening the samples for the CrB8 clubroot resistance locus comprising a molecular marker allele or a haplotype of molecular marker alleles linked to CrB8 clubroot resistance, wherein the marker allele or haplotype of marker alleles are one or more resistance marker alleles shown in SEQ ID NO: 1, 5, 11, 16, 20, 23, 28, 30, 33, or 37 on chromosome N8; and selecting one or more of the progeny plants comprising the CrB8 clubroot resistance locus, thereby obtaining a *Brassica* plant comprising a clubroot resistance locus.

2. The method of claim 1, wherein the CrB8 clubroot resistance locus physical positions on chromosome 8 (Chr 8) corresponds to position 10,656,081 to position 13,303,318 of Chr 8 of reference line DH12075.

3. The method of claim 1, wherein the method comprises screening the sample for the presence of one or more CrB8 resistance marker alleles shown in SEQ ID NO: 1, 5, 11, 16, 20, 23, 28, 30, 33, or 37.

4. The method of claim 3, wherein the method comprises screening the sample for the presence of one or more CrB8 resistance marker alleles shown in SEQ ID NO:23, SEQ ID NO:30, or SEQ ID NO:33, or SEQ ID NO:37.

5. The method of claim 1 further comprising:

crossing the selected one or more progeny plants with the second parent *Brassica* plant to produce backcross progeny plants.

6. The method of claim 5 further comprising:

obtaining a nucleic acid-containing sample from one or more backcross progeny plants;

screening each sample from the backcross progeny plants for a sequence comprising the CrB8 clubroot resistance locus; and selecting one or more backcross progeny plants comprising the CrB8 clubroot resistance locus.

7. The method of claim 6 further comprising:

crossing the selected one or more backcross progeny plants with the second parent *Brassica* plant to produce additional backcross progeny plants;

screening a nucleic acid-containing sample from one or more additional backcross progeny plants for a sequence comprising the CrB8 clubroot resistance locus; and selecting one or more additional backcross progeny plants comprising the CrB8 clubroot resistance locus.

8. The method of claim 7, further comprising repeating steps of screening and selecting additional backcross progeny plants two or more additional times to produce further backcross progeny plants that comprise the CrB8 clubroot resistance locus and the agronomic characteristics of the second parent plant when grown in the same environmental conditions.

9. The method of claim 1, wherein screening each sample comprises the use of a first probe comprising any probe for resistance allele shown in SEQ ID NO: 1, 5, 11, 16, 20, 23, 28, 30, 33, or 37, to thereby detect the presence of a molecular marker allele linked to clubroot resistance.

10. The method of claim 1, wherein screening the sample comprises nucleic acid sequencing, amplification, or both amplification and nucleic acid sequencing.

* * * * *